United States Patent
Salafsky

(10) Patent No.: US 9,395,358 B2
(45) Date of Patent: Jul. 19, 2016

(54) METHODS FOR DETECTING ALLOSTERIC MODULATORS OF PROTEIN

(71) Applicant: BIODESY, INC., South San Francisco, CA (US)

(72) Inventor: Joshua S. Salafsky, San Francisco, CA (US)

(73) Assignee: Biodesy, Inc., South San Francisco, CA (US)

(*) Notice: Subject to any disclaimer, the term of this patent is extended or adjusted under 35 U.S.C. 154(b) by 96 days.

(21) Appl. No.: 14/396,494

(22) PCT Filed: Apr. 25, 2013

(86) PCT No.: PCT/US2013/000117
§ 371 (c)(1),
(2) Date: Oct. 23, 2014

(87) PCT Pub. No.: WO2013/162654
PCT Pub. Date: Oct. 31, 2013

(65) Prior Publication Data
US 2015/0119270 A1    Apr. 30, 2015

Related U.S. Application Data

(63) Continuation-in-part of application No. 13/794,277, filed on Mar. 11, 2013, now abandoned, and a continuation-in-part of application No. PCT/US2012/063286, filed on Nov. 2, 2012.

(60) Provisional application No. 61/638,131, filed on Apr. 25, 2012, provisional application No. 61/638,026, filed on Apr. 25, 2012, provisional application No. 61/595,123, filed on Feb. 5, 2012.

(51) Int. Cl.
*G01N 1/00* (2006.01)
*G01N 33/542* (2006.01)
*G01N 33/543* (2006.01)
*G01N 33/68* (2006.01)

(52) U.S. Cl.
CPC ........ *G01N 33/542* (2013.01); *G01N 33/54306* (2013.01); *G01N 33/68* (2013.01); *G01N 33/6845* (2013.01); *G01N 2333/726* (2013.01); *G01N 2333/91205* (2013.01); *G01N 2333/91215* (2013.01); *G01N 2500/04* (2013.01)

(58) Field of Classification Search
None
See application file for complete search history.

(56) References Cited

U.S. PATENT DOCUMENTS

| | | |
|---|---|---|
| 5,145,790 A | 9/1992 | Mattingly et al. |
| 5,156,810 A | 10/1992 | Ribi |
| 5,236,826 A | 8/1993 | Marshall |
| 5,376,556 A | 12/1994 | Tarcha et al. |
| 5,633,724 A | 5/1997 | King et al. |
| 5,696,157 A | 12/1997 | Wang et al. |
| 5,800,992 A | 9/1998 | Fodor et al. |
| 5,962,248 A | 10/1999 | Tadano et al. |
| 6,055,051 A | 4/2000 | Eisenthal |
| 6,096,497 A | 8/2000 | Bauer |
| 6,180,415 B1 | 1/2001 | Schultz et al. |
| 6,194,222 B1 | 2/2001 | Buechler et al. |
| 6,204,067 B1 | 3/2001 | Simon et al. |
| 6,228,326 B1 | 5/2001 | Boxer et al. |
| 6,284,197 B1 | 9/2001 | Abbott et al. |
| 6,410,245 B1 | 6/2002 | Northrop et al. |
| 6,455,303 B1 | 9/2002 | Orwar et al. |
| 6,456,423 B1 | 9/2002 | Nayfeh et al. |
| 6,699,719 B2 | 3/2004 | Nguyen et al. |
| 6,780,584 B1 | 8/2004 | Edman et al. |
| 6,953,694 B2 | 10/2005 | Salafsky et al. |
| 7,023,547 B2 | 4/2006 | Venkatasubbarao et al. |
| 7,045,337 B2 | 5/2006 | Schultz et al. |
| 7,105,310 B1 | 9/2006 | Gray et al. |
| 7,108,970 B2 | 9/2006 | Levinson |
| 7,545,494 B2 | 6/2009 | Haiml et al. |
| 8,039,270 B2 | 10/2011 | Dultz et al. |
| 8,497,073 B2 | 7/2013 | Salafsky |
| 8,932,822 B1 | 1/2015 | Salafsky |
| 2003/0129649 A1 | 7/2003 | Kobilka et al. |
| 2003/0148391 A1 | 8/2003 | Salafsky |
| 2004/0146460 A1 | 7/2004 | Salafsky |
| 2010/0068144 A1 | 3/2010 | Salafsky |
| 2012/0202296 A1 | 8/2012 | Eisenthal |
| 2013/0129628 A1 | 5/2013 | Pantazis et al. |
| 2014/0113312 A1 | 4/2014 | Salafsky |

(Continued)

FOREIGN PATENT DOCUMENTS

| | | |
|---|---|---|
| EP | 0740156 A1 | 10/1996 |
| EP | 0941474 B1 | 3/2006 |

(Continued)

OTHER PUBLICATIONS

Annis, et al. A general technique to rank protein-ligand binding affinities and determine allosteric versus direct binding site competition in compound mixtures. J Am Chem Soc. Dec. 1, 2004;126(47):15495-503.
Ben-Oren, et al. Infrared nonlinear optical measurements of membrane potential in photoreceptor cells. Biophys J. Sep. 1996;71(3):1616-20.
Berkovic, et al. Interference between second-harmonic generation from a substrate and from an adsorbate layer. Journal of the Optical Society of America B-Optical Physics. 1989; 6:205-208.
Bethea. Experimental technique of dc induced SHG in liquids: measurement of the nonlinearity of CH2I2. Applied Optics. 1975; 14:1447-1451.
Bieri, et al. Micropatterned immobilization of a G protein-coupled receptor and direct detection of G protein activation. Nature Biotechnology. 1999; 17:1105-1108.
Bouevitch, et al. Probing membrane potential with nonlinear optics. Biophys J. Aug. 1993;65(2):672-9.

(Continued)

*Primary Examiner* — Jacob Cheu
(74) *Attorney, Agent, or Firm* — Wilson Sonsini Goodrich & Rosati

(57) ABSTRACT

The present invention discloses, inter alia, methods for labeling a target protein with an SHG-active probe for detection by second harmonic or sum-frequency generation in order to identify agents which bind to an allosteric site on the target protein thereby altering its structural conformation.

21 Claims, 7 Drawing Sheets

(56) References Cited

U.S. PATENT DOCUMENTS

| | | |
|---|---|---|
| 2015/0051110 A1 | 2/2015 | Salafsky et al. |
| 2015/0301048 A1 | 10/2015 | Salafsky |

FOREIGN PATENT DOCUMENTS

| | | |
|---|---|---|
| EP | 1798555 A1 | 6/2007 |
| WO | WO 02/095070 A2 | 11/2002 |
| WO | WO 03/055379 A2 | 7/2003 |
| WO | WO 03/064991 A2 | 8/2003 |
| WO | WO 2011/131747 A1 | 10/2011 |
| WO | WO 2013/115867 A1 | 8/2013 |
| WO | WO 2013/162654 A1 | 10/2013 |
| WO | WO 2014/201435 A1 | 12/2014 |

OTHER PUBLICATIONS

Boyd, et al. Local-field enhancement on rough surfaces with the use of optical 2nd-harmonic generation. Phys. Rev. B 1984; 30:519-526.

Campagnola, et al. High-resolution nonlinear optical imaging of live cells by second harmonic generation. Biophys J. Dec. 1999;77(6):3341-9.

Campagnola, et al. Second-harmonic imaging microscopy for visualizing biomolecular arrays in cells, tissues and organisms. Nat Biotechnol. Nov. 2003;21(11):1356-60.

Campagnola, et al. Three-dimensional high-resolution second-harmonic generation imaging of endogenous structural proteins in biological tissues. Biophysical Journal. 2002; 81:493-508.

Chen, et al. Detection of Molecular Monolayers by Optical Second-Harmonic Generation. Physical Review Letters. 1981; 46:1010-1012.

Clark, et al. Second harmonic generation properties of fluorescent polymer-encapsulated gold nanoparticles. J. Am. Chem. Soc. 2000; 122:10234-10235.

Clarke, et al. Conformational changes of fibrinogen after adsorption. Journal of Physical Chemistry B. 2005; 109:22027-22035.

Clays, et al. Nonlinear optical properties of proteins measured by hyper-rayleigh scattering in solution. Science. Nov. 26, 1993;262(5138):1419-22.

Cohen, et al. A Fluorescent Probe Designed for Studying Protein Conformational Change. PNAS. 2005; 102(4):965-970.

Conboy, et al. Studies of Alkane/water interfaces by total internal reflection second harmonic generation. J. Phys. Chem. 1994; 98:9688-9698.

Delprincipe et al. Two Photo and UV-Laser Flash Photlysis of CA Cage Dimethoynitrophenyl-EGTA-4. Cell Calcium. 1999; 25:85-91.

Ditcham, et al. An immunosensor with potential for the detection of viral antigens in body fluids, based on surface second harmonic generation. Biosens Bioelectron. May 2001;16(3):221-4.

Dworczak, et al. Electric field induced second harmonic generation (EFISH) experiments in the swivel cell: new aspects of an established method. Phys. Chem. Chem. Phys., 2000; 2:5057-5064.

Eisenthal. Photochemistry and photophysics of liquid interfaces by second harmonic spectroscopy. J. Phys. Chem. 1996; 100:12997-13006.

European search report Jan. 24, 2008 for EP Application No. 03736879.2.

European search report May 18, 2005 for EP Application No. 01995403.1.

European search report Dec. 3, 2004 for EP Application No. 01957166.0.

Fejer, et al. Quasi-Phase-Matched Second Harmonic Generation Tuning and Tolerances. IEEE Journal of Quantum Electronics. 1992; 28(11):2631-2654.

Felderhof, et al. Optical second-harmonic generation from adsorbate layers in total-reflection geometry. Journal of the Optical Society of America B-Optical Physics. 1993; 10:1824-1833.

Feller, et al. Investigation of surface-induced alignment liquid-crystal molecules by optical second-harmonic generation. Physical Review A. 1991; 43(12), 6778-6792.

Finn, et al. Measurements of hyperpolarizabilities for some halogenated methanes. J. Chem. Phys. 1974; 60:454-458.

Fittinghoff. Collinear type II second-harmonic-generation frequency-resolved optical gating for use with high-numerical-aperature objectives, 1998, Opt Lett, 23(13), 1046-1048.

Galletto, et al. Enhancement of second harmonic response by adsorbates on gold colloids: the effect of aggregation. J. Phys. Chem. B. 1999; 103:8706-8710.

Ghanouni, et al. Agonist-induced conformational changes in the G-protein-coupling domain of the beta 2 adrenergic receptor. Proc Natl Acad Sci U S A. May 22, 2001;98(11):5997-6002. Epub May 15, 2001.

Ghanouni, et al. Functionally Different Agonists Induce Distinct Conformations in the G Protein Coupling Domain of the B2 Adrenergic Receptor. Journal of Biological Chemistry. 2001; 276:24433-24436.

Goh, et al. Absolute Orientation of Water-Molecules at the Neat Water-Surface. Journal of Physical Chemistry. 1988; 92:5074-5075.

Groves, et al. Micropatterning fluid bilayers on solid supports. Science. 1997; 275:651653.

Harrick. Internal reflection spectroscopy. Hulick Scientific Corporation. 2nd printing 1979.

Heinz, et al. Spectroscopy of Molecular Monolayers by Resonant Second-Harmonic Generation. Phys. Rev. Lett. 1982; 48, 478. DOI: http://dx.doi.org/10.1103/PhysRevLett.48.478.

Heinz. Determination of molecular orientation of monlayer adsorbates by optical second-harmonic generation. Physical Review A. 1991; 28(3):1883-1885.

Huang, et al. Nonlinear optical properties of potential sensitive styryl dyes. Biophys J. May 1988;53(5):665-70.

Hubbard, et al. Nonlinear optical studies of a fluorinated poled polyimide guest-host system. Applied Physics Letters. 1994; 65(3):265-267.

International search report dated Jan. 22, 2002 for PCT/US2001/022411.

International search report dated Feb. 10, 2006 for PCT/US2003/017807.

International search report dated Mar. 23, 2006 for PCT/US2002/022681.

International search report dated Apr. 20, 2012 for PCT/US2012/030010.

International search report dated May 1, 2002 for PCT/US2001/046932.

International search report dated Oct. 20, 2001 for PCT/US2001/022412.

Jager, et al. Comparison of quasi-phase-matching geometries for second harmonic generation in poled polymer channel waveguides at 1.5 mm,. Appl. Phys. Lett.1996; 68:1183-1185.

Kajikawa, et al. Second harmonic generation in disperse-red-labeled poly(methyl methacrylate) Langmuir Blodgett film. Appl. Phys. Letters. May 3, 1993; 62(18):2161-2163.

Kemnitz, et al. The Phase of 2nd-Harmonic Light Generated at an Interface and Its Relation to Absolute Molecular-Orientation. Chemical Physics Letters. 1986; 131:285-290.

Khatchatouriants, et al. GFP is a selective non-linear optical sensor of electrophysiological processes in Caenorhabditis elegans. Biophys J. Nov. 2000;79(5):2345-52.

Kriech, et al. Using the intrinsic chirality of a molecule as a label-free probe to detect molecular adsorption to a surface by second harmonic generation. Applied Spectroscopy. 2005; 59:46-753.

Levine, et al. Absolute signs of hyperpolarizabilities in the liquid state. J. Chem. Phys. 1974; 60(10)3856-3858.

Levine, et al. Charge transfer complexes and hyperpolarizabilities. J. Chem. Phys. 1977; 66:1070-1074.

Levine, et al. Molecular hyperpolarizabilities determined from conjugated and nonconjugated organic liquids. Appl. Phys. Lett. 1974; 24:445-447.

Levine, et al. Second and third order hyperpolarizabilities of organic molecules. J. Chem. Phys. 1975; 63(6):2666-2682.

Levine, et al. Second Order Hyperpolarizability of a Polypeptide a-helix: Poly--y-benzyl-L-glutamate. J. Chem. Phys. 1976; 65(5):1989-1993.

Levine, et al. Ultraviolet dispersion of the donor-acceptor charge transfer contribution to the second order hyperpolarizability. J. Chem. Phys. 1978; 69(12): 5240-5245.

(56) References Cited

OTHER PUBLICATIONS

Levine. Conjugated electron contributions to the second order hyperpolarizability of substituted benzene molecules J. Chem. Phys. 1975; 63:115-117.
Lewis, et al. Second Harmonic Generation of Biological Interfaces: Probing the Membrane Protein Bacteriorhodopsin and Imaging Membrane Potential Around GFP Molecules at Specific Sites in Neuronal Cells of C. elegans. Chemical Physics. 1999; 245:133-144.
MacBeath, et al. Printing Proteins as Microarrays for High-Throughput Function Determination. Science. 2000; 289:1760-1763.
McConnell, et al. Electronic and optical properties of chemically modified metal nanoparticles and molecularly bridged nanoparticle arrays. J. Phys. Chem. B. 2000; 104: 8925-8930.
Millard, et al. Second harmonic imaging microscopy. Methods Enzymol. 2003;361:47-69.
Moreaux, et al. Membrane imaging by second harmonic generation microscopy.
Notice of Allowance mailed on May 6, 2013 for U.S. Appl. No. 12/571,342, filed on Sep. 30, 2009, 9 pages.
Notice of Allowance mailed on Oct. 10, 2014 for U.S. Appl. No. 14/482,899, filed on Sep. 10, 2014, 12 pages.
Office action dated Jan. 30, 2015 for U.S. Appl. No. 13/834,521.
Office action dated Feb. 7, 2002 for U.S. Appl. No. 09/731,366.
Office action dated Feb. 16, 2011 for U.S. Appl. No. 12/571,342.
Office action dated Feb. 16, 2012 for U.S. Appl. No. 12/571,342.
Office action dated Feb. 23, 2004 for U.S. Appl. No. 09/731,366.
Office action dated Mar. 24, 2008 for U.S. Appl. No. 11/327,199.
Office action dated Mar. 30, 2009 for U.S. Appl. No. 11/327,199.
Office action dated Apr. 14, 2015 for U.S. Appl. No. 13/834,809.
Office action dated Apr. 21, 2004 for U.S. Appl. No. 09/907,038.
Office action dated Apr. 21, 2015 for U.S. Appl. No. 13/838,340.
Office action dated Apr. 21, 2015 for U.S. Appl. No. 13/838,491.
Office action dated Jun. 18, 2007 for U.S. Appl. No. 11/327,199.
Office action dated Aug. 25, 2003 for U.S. Appl. No. 09/907,035.
Office action dated Sep. 10, 2004 for U.S. Appl. No. 09/731,366.
Office action dated Sep. 15, 2015 for U.S. Appl. No. 13/834,521.
Office action dated Sep. 20, 2005 for U.S. Appl. No. 10/467,098.
Office action dated Sep. 25, 2015 for U.S. Appl. No. 13/838,753.
Office action dated Oct. 2, 2012 for U.S. Appl. No. 12/571,342.
Office action dated Oct. 23, 2003 for U.S. Appl. No. 09/731,366.
Office action dated Oct. 28, 2002 for U.S. Appl. No. 09/731,366.
Office action dated Nov. 3, 2006 for U.S. Appl. No. 10/970,754.
Office action dated Nov. 20, 2002 for U.S. Appl. No. 09/907,035.
Oral Abstracts from the Society of Biomolecular Sciences 14th Annual Conference and Exhibition: St. Louis, Missouri Apr. 6-10, 2008. J. Biomol Screen 2008 13: 692. DOI: 10.1177/1087057108322219.
Oudar, et al. Hyperpolarizabilities of the nitroanilines and their relations to the excited state dipole moment. J. Chem. Phys. 1977; 66. 2664-2668.
Oudar, et al. Optical nonlinearities of conjugated molecules. Stilbene derivatives and highly polar aromatic compounds. J. Chem. Phys. 1977; 67(2):446-457.
Paige, et al. Estrogen receptor (ER) modulators each induce distinct conformational changes in ER alpha and ER beta. Proc Natl Acad Sci U S A. Mar. 30, 1999;96(7):3999-4004.
Paszti, et al. Sum frequency generation vibrational spectroscopy studies of protein adsorption on oxide-covered Ti surfaces. Journal of Physical Chemistry B. 2004; 108:7779-7787.
Peleg, et al. Nonlinear optical measurement of membrane potential around single molecules at selected cellular sites. Proc Natl Acad Sci U S A. Jun. 8, 1999;96(12):67004.
Pitchford, et al. Direct, real-time detection of kinae type II inhibitors using second harmonic generation (SHG) detection. 2011. Poster T380. Retrieved Apr. 18, 2012. www.labautopedia.com/mw/images/T380posterSBS2011.jpg.
Polizzi, et al. (2004). Ellipsometric approach for the real-time detection of label-free protein absroption by second harmonic generation. Journal of the American Chemical Society. 2004; 126:5001-5007.
Reider, et al. Second-order Nonlinear Optical Effects at Surfaces and Interfaces in Photonic Probes of Surfaces. Halevia, P., editor. Elsevier Science, Amsterdam. Chapter 9. 1995. 415-478.
Request for Continued Examination filed on Jan. 13, 2009 for U.S. Appl. No. 11/327,199, filed on Jan. 5, 2006, 6 pages.
Request for Continued Examination filed on Jul. 16, 2012 for U.S. Appl. No. 12/571,342, filed on Sep. 30, 2009, 10 pages.
Response to Non-Final Office Action filed on Apr. 1, 2013 for U.S. Appl. No. 12/571,342, filed on Sep. 30, 2009, 9 pages.
Response to Non-Final Office Action filed on Aug. 18, 2011 for U.S. Appl. No. 12/571,342, filed on Sep. 30, 2009, 6 pages.
Response to Non-Final Office Action filed on Dec. 14, 2007 for U.S. Appl. No. 11/327,199, filed on Jan. 5, 2006, 8 pages.
Rinuy, et al. Second harmonic generation of glucose oxidase at the air/water interface. Biophysial Journal. 1999; 77:3350-3355.
Rodriguez, et al. In vivo incorporation of multiple unnatural amino acids through nonsense and frameshift suppression. Proc Natl Acad Sci U S A. Jun. 6, 2006;103(23):8650-5. Epub May 25, 2006.
Salafsky, et al. A second-harmonic-active unnatural amino acid as a structural probe of biomolecules on surfaces. J. Phys. Chem. B, 2008, 112 (47), pp. 15103-15107.
Salafsky, et al. Protein absorption at interfaces detected by second-harmonic generation. Journal of Physical Chemistry B. 2000; 104:7752-7755.
Salafsky, et al. Protein absorption at interfaces detected by second-harmonic generation. J. Phys. Chem. B. 2004; 108(10):3376. Additions and Corrections.
Salafsky, et al. Second Harmonic Spectroscopy: Detection and Orientation of Molecules at a Biomembrane Interface. Chemical Physics Letters 2000; 319:435-439.
Salafsky, et al. SHG labels for detection of molecules by second harmonic generation. Chemical Physics Letters. 2001; 342:485-491.
Salafsky, J. (Apr. 2008). "Second-Harmonic Generation (SHG) for Identification of Allosteric D & Conformation-Specific Compounds" PowerPoint Presentation presented to SBS, 30 pages.
Salafsky, J. (Apr. 15, 2009). "Detection Method for Conformational Change Second-Harmonic Generation Provides a Molecular-Level, Functional Readout in Real Time" Gen Eng & Biotech News, 2 pages.
Salafsky. Detection of protein conformational change by optical second-harmonic generation. J Chem Phys. Aug. 21, 2006;125(7):074701.
Salafsky. Second-harmonic generation as a probe of conformational change in molecules. Chemical Physics Letters. 2003; 381(5):705-709.
Salafsky. Second-harmonic generation for studying structural motion of biological molecules in real time and space. Phys Chem Chem Phys. Nov. 14, 2007;9(42):5704-11. Epub Sep. 7, 2007.
Samanta, et al. Excited state dipole moment of PRODAN as determined from transient dieletric loss measurements. Journal of Physical Chemistry A. 2000; 104:8972-8975.
Seok, et al. Topology of allosteric regulation of lactose permease. Proc Natl Acad Sci U S A. Dec. 9, 1997;94(25):13515-9.
Shen. Optical Second Harmonic Generation at Interfaces. Annual Review of Physical Chemistry. 1989; 40(1):327-350.
Shen. The Principles of Nonlinear Optics, John Wiley & Sons, New York. 1984.
Shen.. Surface properties probed by second-harmonic and sum-frequency generation. Nature. 1989; 337: 20 519-525.
Simard, et al. A new screening assay for allosteric inhibitors of cSrc. Nat Chem Biol. Jun. 2009;5(6):394-6. doi: 10.1038/nchembio.162. Epub Apr. 26, 2009.
Simard, et al. Development of a fluorescent-tagged kinase assay system for the detection and characterization of allosteric kinase inhibitors. J Am Chem Soc. Sep. 23, 2009;131(37):13286-96. doi: 10.1021/ja902010p.
Singer, et al. Measurements of molecular second-order optical susceptibilities using dc-induced second harmonic generation. J. Chem. Phys. 1981; 75:3572-3580.
Summerer, et al. A genetically encoded fluorescent amino acid. Proc Natl Acad Sci U S A. Jun. 27, 2006;103(26):9785-9. Epub Jun. 19, 2006.

(56) References Cited

OTHER PUBLICATIONS

Theodossiou, et al. Thermally Induced Irreversible Conformational Changes in Collagen Probed by Optical Second Harmonic Generation and Laser-induced Fluorescence, 2002; 17:34-41.

Wang, et al. In situ, nonlinear optical probe of Surfactant Adsorption on the Surface of Microparticles in Colloids. Langmuir 2000, 16, 2475-2481.

Wang, et al. Polarity of liquid interfaces by second harmonic generation spectroscopy, 1997, J Phys Chem A, 101, 713-718.

Weidner, et al. Sum frequency generation and solid-state NMR study of the structure, orientation, and dynamics of polystyrene-adsorbed peptides. Proc Natl Acad Sci U S A. Jul. 27, 2010;107(30):13288-93. doi: 10.1073/pnas.1003832107. Epub Jul. 13, 2010.

Yang, et al. Surface second harmonic generation (SSHG)—a new scheme for immunoassay. Proceedings of the SPIE. 1996; 2676:290-296. http://dx.doi.org/10.1117/12.238808.

Office action dated Feb. 4, 2016 for U.S. Appl. No. 14/548,804.

European search report and opinion dated May 4, 2015 for EP Application No. 13781743.3.

Hall, et al. The structural basis for the transition from Ras-GTP to Ras-GDP. Proc Natl Acad Sci U S A. Sep. 17, 2002;99(19):12138-42. Epub Sep. 4, 2002.

International preliminary report on patentability dated Oct. 3, 2013 for PCT/US2012/030010.

International search report and written opinion dated Apr. 20, 2012 for PCT/US2012/030010.

International search report and written opinion dated Dec. 21, 2012 for PCT/US2012/063286.

International search report dated Jun. 27, 2013 for PCT/US2013/000117.

Martin, et al. A novel apporach to the discovery of small-molecule ligands of CDK2. Chembiochem. Sep. 24, 2012;13(14):2128-36. doi: 10.1002/cbic.201200316. Epub Aug. 14, 2012.

Notice of allowance dated Jun. 18, 2014 for U.S. Appl. No. 13/794,277.

Notice of allowance dated Oct. 10, 2014 for U.S. Appl. No. 14/482,899.

NSF. SBIR Phase I: Development of a Conformational Screen for Rapidly Identifying Kinase Inhibitor Type Using SHG. NSF SBIR grant abstract. 2011.

Salaf Sky, et al. SHG labels for detection of molecules by second harmonic generation. Chemical Physics Letters. 2001; 342:485-491.

Salafsky, J. (Apr. 15, 2009). "Detection Method for Conformational Change Second- Harmonic Generation Provides a Molecular-Level, Functional Readout in Real Time" Gen Eng & Biotech News, 2 pages.

Salafsky. Real-time detection of GPCR conformational change. NIH grant abstract. 2005.

Salafsky. Real-time measurement of protein conformational change in key therapeutic targets: applications to Abl-kinase and mutant Ras. Biodesy, LLC. SLAS Conference. PPT presentation. Feb. 7, 2012.

Salafsky. Second-harmonic generation (SHG) for allosteric drug discovery: conformational change in real time. Biodesy, LLC. Wmen Conference. PPT presentation. May 9, 2012.

Salafsky. Second-Harmonic Generation (SHG) for Identification of Allosteric and Conformation-Specific Compounds. Journal of Biomolecular Screening. 2008; 13(7):697.

Schneider, et al. Direct binding assay for the detection of type IV allosteric inhibitors of Abl. J Am Chem Soc. Jun. 6, 2012;134(22):9138-41. doi: 10.1021/ja303858w. Epub May 25, 2012.

A.

METHODS FOR DETECTING ALLOSTERIC MODULATORS OF PROTEIN

CROSS-REFERENCE TO RELATED APPLICATIONS

This application is filed pursuant to 35 U.S.C. §371 as a United States National Phase Application of International Application No. PCT/US2013/000117, filed Apr. 25, 2013, which claims the benefit of U.S. Provisional Application No. 61/638,131, filed Apr. 25, 2012 and U.S. Provisional Patent Application No. 61/638,026, filed Apr. 25, 2012. International Application No. PCT/US2013/000117 also is a continuation-in-part of U.S. application Ser. No. 13/794,277, filed Mar. 11, 2013, which claims the benefit under 35 U.S.C. §119(e) of U.S. Application No. 61/638,131, filed Apr. 25, 2012, and is a continuation-in-part of International Application No. PCT/US2012/063286, filed Nov. 2, 2012, which claims the benefit of U.S. Provisional Application No. 61/638,026, filed Apr. 25, 2012 and U.S. Provisional Application No. 61/595,123, filed Feb. 5, 2012. The foregoing applications are incorporated by reference herein for all purposes.

FIELD OF THE INVENTION

The invention relates to the field of molecular detection and protein detection in particular. Specifically, provided herein are methods for identifying and detecting allosteric modulators of target proteins using second harmonic generation technology.

BACKGROUND OF THE INVENTION

The number of potential therapeutic targets in cancer biology has grown exponentially over the last twenty years with the advancement of the understanding of cancer genomics. In that same time, however, the number of approved therapies which target the most abundantly activated cancer-related genes has grown only marginally. Many cancer targets that are attractive from a biological perspective are considered intractable ("undruggable") from a chemical standpoint. There is a growing understanding that these protein targets are not amenable to conventional drug discovery approaches, typically because they possess a relatively large contact area when interacting with other proteins (i.e., protein-protein interactions or "PPI") or due to the fact that they possess a ligand that binds extremely tightly to the active site of the protein. An example of the latter case is found with proteins such as Ras which binds its ligand GTP with picomolar affinity making competition with potential drugs difficult. It is estimated that 75-80% of all existing targets are beyond the reach of the classical small molecule or biologic (protein) classes of therapeutics, which generally inhibit protein function by competitively binding to the protein's active site, among them a number of highly validated targets for cancer.

Allosteric modulators for such "undruggable" targets offer an attractive therapeutic solution. By definition, allosteric molecules bind to a site other than a protein's active site thereby changing the protein's conformation with a concomitant functional effect (e.g., inhibition, activation of a receptor, etc.). Additionally, among other advantages (1), allosteric modulation of target proteins has the added benefit of not having to rely on inhibition or competition with the binding of the natural ligand to the protein, which can result in unintended clinical side effects. However, it has been difficult to identify allosteric modulators using currently available conventional techniques. For example, structural information obtained from X-ray crystallography or NMR methods is limited for drug discovery purposes due to low throughput, sensitivity, non-physiological conditions, size of the protein amenable to the technique, and many other factors. What is needed, therefore, are techniques to identify agents capable of allosterically modulating the structure of a target protein rapidly and in a high-throughput manner.

Such techniques are provided herein by the disclosure of methods for identifying agents capable of allosterically binding to a target protein thereby altering its conformational structure.

Throughout this specification, various patents, patent applications and other types of publications (e.g., journal articles) are referenced. The disclosure of all patents, patent applications, and publications cited herein are hereby incorporated by reference in their entirety for all purposes.

BRIEF SUMMARY OF THE INVENTION

The invention provided herein discloses, inter alia, methods for identifying and detecting allosteric modulators of target protein conformational states through the use of second harmonic generation technology.

Accordingly, in some aspects, provided herein are methods for identifying an agent B that binds to an allosteric site on a target protein, the method comprising: (a) contacting the target protein with an agent A that binds to an active site of the target protein; (b) contacting the target protein with the agent B, wherein the target protein is labeled with a second harmonic-active moiety (such as, a label) having a net orientation at an interface, wherein a detectable signal is generated by the second harmonic-active moiety (such as, a label) using a surface selective technique, and wherein the detectable signal indicates a conformational change in the structure of the target protein produced when the agent B binds to an allosteric site on the target protein; and (c) measuring the presence or absence of the detectable signal after the target protein has been contacted with the agent B. In some embodiments, the second harmonic-active moiety (such as, a label) is selected from the group consisting of PyMPO-MALEIMIDE™ (1-(2-Maleimidylethyl)-4-(5-(4-Methoxyphenyl)Oxazol-2-yl)Pyridinium Methanesulfonate), PyMPO-NHS, PyMPO-succinimidyl ester, BADAN™ (6-Bromoacetyl-2-Dimethylaminonaphthalene), and ACRYLODAN™ (6-Acryloyl-2-Dimethylaminonaphthalene). In some embodiments, the second harmonic-active moiety (such as, a label) is bound to the target protein by one or more sulfhydryl groups on the surface of the target protein. In some embodiments, said one or more sulfhydryl groups are native sulfhydryl groups. In some embodiments, said one or more sulfhydryl groups are engineered sulfhydryl groups. In some embodiments, said one or more sulfhydryl groups are located on target protein amino acid residues known to contact one or more ligand. In some embodiments of any of the embodiments described herein, the second harmonic-active moiety (such as, a label) is PyMPO-MALEIMIDE™ (1-(2-Maleimidylethyl)-4-(5-(4-Methoxyphenyl)Oxazol-2-yl)Pyridinium Methanesulfonate). In some embodiments, the second harmonic-active moiety (such as, a label) is bound to the target protein by one or more amine groups on the surface of the target protein. In some embodiments, said one or more amine groups are native amine groups. In some embodiments, said one or more amine groups are engineered amine groups. In some embodiments of any of the embodiments described herein, said one or more amine groups are located on target protein amino acid residues known to contact one or more one or more ligands. In some embodiments of any of the embodiments described herein, the second harmonic-active moiety (such as, a label) is PyMPO-succinimidyl ester. In some embodiments of any of the embodiments described herein, the target protein is labeled in situ while bound to a surface. In some embodiments, the second harmonic-active moiety (such as, a label) is an unnatural amino acid. In some embodiments, the unnatural amino acid is located in a region of the target protein known to contact one or more ligands. In some embodiments, the unnatural amino acid is Aladan. In some embodiments of any of the embodiments described herein, the ligand is one or more of a protein, a nucleic acid, a phospholipid, a carbohydrate, or a co-factor. In some embodiments, the ligand is a protein member of a kinase signaling cascade. In some embodiments, the target protein is a G protein-coupled receptor, a steroid hormone receptor, or a tyrosine kinase receptor. In some embodiments of any of the embodiments described herein, the interface is selected from the group consisting of: a glass surface, a polyethylene glycol surface, a supported lipid bilayer surface, a lipid analog bilayer surface, a plastic surface, a metal surface, a latex surface, a rubber surface, a ceramic surface, a polymeric surface, a polypropylene surface, a polyvinylidene difluoride surface, a polyethylene surface. In some embodiments, the surface is derivatized with oligo-PEG molecules or lipids. In some embodiments, the oligo-PEG molecules or lipids are Ni-NTA-bearing oligo-PEG molecules or Ni-NTA-bearing lipids. In some embodiments, the surface is a supported lipid bilayer or a lipid analog bilayer. In some embodiments of any of the embodiments described herein the target protein comprises an affinity tag. In some embodiments of any of the embodiments described herein the conformational change in the structure of the target protein is detected in real time. In some embodiments of any of the embodiments described herein the agent A and/or the agent B is a small molecule chemical compound, an antibody, a non-antibody polypeptide, a carbohydrate, an inhibitory nucleic acid, or any combination thereof.

In some aspects, provided herein is a method for identifying a specific site in the structure of a target protein that undergoes a conformational change upon binding to an agent, the method comprising: (a) contacting the target protein with the agent, wherein the target protein is labeled at a first amino acid residue with a second harmonic-active moiety (such as, a label) having a net orientation at an interface, wherein a first detectable signal is generated by the second harmonic-active moiety (such as, a label) using a surface selective technique, and wherein the first detectable signal indicates a conformational change in the structure of the target protein produced when the agent binds to a site on the target protein; (b) contacting the target protein with the agent, wherein the target protein is labeled at a second amino acid residue with a second harmonic-active moiety (such as, a label) having a net orientation at an interface, wherein the second amino acid residue is located in a region of the target protein that differs from the location of the first amino acid residue, wherein a second detectable signal is generated by the second harmonic-active moiety (such as, a label) using a surface selective technique, and wherein the second detectable signal indicates a conformational change in the structure of the target protein produced when the agent binds to a site on the target protein; and (c) comparing the first detectable signal with the second detectable signal, wherein a conformational change at the site of the first amino acid residue alone indicates that the agent binds to the target protein and induces a conformational change to the structure of the protein at the site of the first amino acid residue, and wherein a conformational change at the site of the second amino acid residue alone indicates that the agent binds to the target protein at the site of the second amino acid residue and induces a conformational change to the structure of the protein at the site of the second amino acid residue. In another aspect, provided herein is a method for identifying a site-specific conformational change in the structure of a protein upon binding of an agent to the protein, the method comprising: (a) contacting the target protein with the agent, wherein the target protein is labeled at a first amino acid residue with a second harmonic-active moiety having a net orientation at an interface, wherein a first detectable signal is generated by the second harmonic-active moiety using a surface selective technique, and wherein the first detectable signal indicates a conformational change in the structure of the target protein produced when the agent binds to a site on the target protein; (b) contacting the target protein with the agent, wherein the target protein is labeled at a second amino acid residue with a second harmonic-active moiety having a net orientation at an interface, wherein the second amino acid residue is located in a region of the target protein that differs from the location of the first amino acid residue, wherein a second detectable signal is generated by the second harmonic-active moiety using a surface selective technique, and wherein the second detectable signal indicates a conformational change in the structure of the target protein produced when the agent binds to a site on the target protein; and (c) comparing the first detectable signal with the second detectable signal, wherein a conformational change at the site of the first amino acid residue alone indicates that the agent induces a conformational change to the structure of the protein at the site of the first amino acid residue and wherein a conformational change at the site of the second amino acid residue alone indicates that the agent induces a conformational change to the structure of the protein at the site of the second amino acid residue. In some embodiments, the method includes the initial step of contacting the target protein with an agent that binds to the active site of the target protein. In some embodiments, the method further comprises repeating steps (b) and (c), wherein one or more additional amino acid residues located at one or more different sites in the target protein are labeled with a second harmonic-active moiety (such as, a label) having a net orientation at an interface, wherein one or more additional detectable signals are generated by the second harmonic-active moieties (such as labels) using a surface selective technique, and wherein the one or more additional detectable signals indicates a conformational change in the structure of the target protein produced when the agent binds to a site on the target protein. In some embodiments of any of the embodiments described herein, the method further comprises determining whether the agent specifically or non-specifically binds to an allosteric site on the target protein, wherein the agent specifically binds to an allosteric site on the target protein if the agent induces a conformational change in the structure of the target protein at the site of one second harmonic-active moiety-labeled amino acid but does not induce a conformational change in the structure of the target protein at the site of one or more other second harmonic moiety-labeled amino acids, and wherein the agent non-specifically binds to an allosteric site on the target protein if the agent induces an identical conformational change in the structure of the target protein at the sites of all second harmonic-active moiety-labeled amino acids. In some embodiments of any of the embodiments described herein, the second harmonic-active moiety (such as, a label) is selected from the group consisting of PyMPO-MALEIMIDE™ (1-(2-Maleimidylethyl)-4-(5-(4-Methoxyphenyl)Oxazol-2-yl)Pyridinium Methanesulfonate), PyMPO-NHS, PyMPO-succinimidyl ester, BADAN™ (6-Bromoacetyl-2-Dimethylaminonaphthalene), and ACRYLODAN™ (6-Acryloyl-2-Dimethylaminonaphthalene). In some embodiments of any of the embodiments described herein, the second harmonic-active moiety (such as, a label) is bound to the target protein by one or more sulfhydryl groups on the surface of the target protein. In some embodiments, said one or more sulfhydryl groups are native sulfhydryl groups. In some embodiments, said one or more sulfhydryl groups are engineered sulfhydryl groups. In some embodiments of any of the embodiments described herein, said one or more sulfhydryl groups are located on target protein amino acid residues known to contact one or more ligand. In some embodiments of any of the embodiments described herein the second harmonic-active moiety (such as, a label) is PyMPO-MALEIMIDE™ (1-(2-Maleimidylethyl)-4-(5-(4-Methoxyphenyl)Oxazol-2-yl)Pyridinium Methanesulfonate). In some embodiments of any of the embodiments described herein the second harmonic-active moiety (such as, a label) is bound to the target protein by one or more amine groups on the surface of the target protein. In some embodiments, said one or more amine groups are native amine groups. In some embodiments, said one or more amine groups are engineered amine groups. In some embodiments of any of the embodiments described herein said one or more amine groups are located on target protein amino acid residues known to contact one or more one or more ligands. In some embodiments, the second harmonic-active moiety (such as, a label) is PyMPO-succinimidyl ester. In some embodiments of any of the embodiments described herein, the target protein is labeled in situ while bound to a surface. In some embodiments, the second harmonic-active moiety (such as, a label) is an unnatural amino acid. In some embodiments, the unnatural amino acid is located in a region of the target protein known to contact one or more ligands. In some embodiments of any of the embodiments described herein, the unnatural amino acid is Aladan. In some embodiments of any of the embodiments described herein, the ligand is one or more of a protein, a nucleic acid, a phospholipid, a carbohydrate, or a co-factor. In some embodiments, the ligand is a protein member of a kinase signaling cascade. In some embodiments, the target protein is a G protein-coupled receptor, a steroid hormone receptor, or a tyrosine kinase receptor. In some embodiments of any of the embodiments described herein, the interface is selected from the group consisting of: a glass surface, a polyethylene glycol surface, a supported lipid bilayer surface, a lipid analog bilayer surface, a plastic surface, a metal surface, a latex surface, a rubber surface, a ceramic surface, a polymeric surface, a polypropylene surface, a polyvinylidene difluoride surface, a polyethylene surface. In some embodiments, the surface is derivatized with oligo-PEG molecules or lipids. In some embodiments, the oligo-PEG molecules or lipids are Ni-NTA-bearing oligo-PEG molecules or Ni-NTA-bearing lipids. In some embodiments, the surface is a supported lipid bilayer or a lipid analog bilayer. In some embodiments of any of the embodiments described herein, the target protein comprises an affinity tag. In some embodiments of any of the embodiments described herein, the conformational change in the structure of the target protein is detected in real time. In some embodiments of any of the embodiments described herein, the agent is a small molecule chemical compound, an antibody, a non-antibody polypeptide, a carbohydrate, an inhibitory nucleic acid, or any combination thereof.

In some aspects, provided herein is a method for identifying an agent that binds to an allosteric site on a G protein-coupled receptor (GPCR), the method comprising (a) contacting the GPCR with a natural ligand, wherein the natural ligand is labeled with a second harmonic-active moiety (such as, a label), wherein the label has a net orientation at an interface upon binding to the GPCR; (b) contacting the GPCR with the agent, wherein a detectable signal is generated by the second harmonic-active moiety (such as, a label) using a surface selective technique, and wherein the detectable signal indicates a conformational change in the structure of the GPCR produced when the agent bind to an allosteric site on the GPCR; and (c) measuring the presence or absence of the detectable signal after the target protein has been contacted with the agent. In some embodiments, the GPCR is located on the surface of a biological cell, a liposome, or a synthetic biological membrane. In other aspects, provided herein is a method for identifying an agent that binds to an allosteric site on a G protein-coupled receptor (GPCR), the method comprising: (a) contacting the GPCR with a known ligand, wherein the known ligand is known to bind to the GPCR, wherein the known ligand is labeled with a second harmonic active moiety, and wherein the labeled ligand has a net orientation at an interface upon binding to the GPCR; (b) contacting the GPCR with the agent, wherein a detectable signal is generated by the second harmonic active label using a surface selective technique, and wherein the detectable signal indicates a conformational change in the structure of the GPCR produced when the agent binds to a site on the GPCR; and (c) measuring the presence or absence of the detectable signal after the target protein has been contacted with the agent. In some embodiments, the biological cell expresses the GPCR naturally. In some embodiments, the biological cell comprises a heterologous nucleic acid encoding the GPCR. In some embodiments of any of the embodiments described herein, the GPCR is selected from the group consisting of alpha-1 adrenegic receptors ($\alpha$1-AR), urotensin (UT) receptors, 5-HT2 and 5-HT6 serotonin receptors, hypocretic (orexin) receptors, histamine HI receptors, bradykinin B1 and B2 receptors, bombesin BB2 receptors, P2Y purinergic receptors, acetycholine receptors, mGluR5 glutamate receptors, vasopressin V2 and VI receptors, angiotensin AGTR1 receptors, cholecystokinin CCKAR and CCKBR receptors, endothelin ENDRA receptors, ghrelin GHSR1a receptors, melatonin MTNR1 A receptors, neurotensin NTSR1 receptors, platelet-activating factor PTAFR receptors, prolactin releasing peptide receptor PRLHR receptors, G-coupled 5-$HT_2$, 5-$HT_{2A}$, 5-$H_{T6}$, and 5-$H_{T7}$ serotonin receptors, $G_i$-coupled GABA-B, histamine H3, and mGluR2/4 glutamate receptors.

In other aspects, provided herein is a method for identifying an agent B that binds to an allosteric site on a target protein, the method comprising: (a) contacting the target protein with an agent A that binds to an active site of the target protein, wherein the agent A is labeled with a second harmonic-active moiety (such as, a label) having a net orientation at an interface, wherein a detectable signal is generated by the second harmonic-active moiety (such as, a label) using a surface selective technique, and wherein the detectable signal indicates a conformational change in the structure of the target protein produced when an agent B binds to an allosteric site on the target protein; (b) contacting the target protein with the agent B; and (c) measuring the presence or absence of the detectable signal after the target protein has been contacted with the agent B. In some aspects, the second harmonic-active moiety (such as, a label) is selected from the group consisting of PyMPO-MALEIMIDE™ (1-(2-Maleimidylethyl)-4-(5-(4-Methoxyphenyl)Oxazol-2-yl)Pyridinium Methanesulfonate), PyMPO-NHS, PyMPO-succinimidyl ester, BADAN™ (6-Bromoacetyl-2-Dimethylaminonaphthalene), and ACRYLODAN™ (6-Acryloyl-2-Dimethylaminonaphthalene). In some embodiments, the second harmonic-active moiety (such as, a label) is bound to the agent A by one or more sulfhydryl groups on the surface of the agent A. In some embodiments, said one or more sulfhydryl groups are native sulfhydryl groups. In some embodiments, said one or more sulfhydryl groups are engineered sulfhydryl groups. In some embodiments, the second harmonic-active moiety (such as, a label) is PyMPO-MALEIMIDE™ (1-(2-Maleimidylethyl)-4-(5-(4-Methoxyphenyl)Oxazol-2-yl)Pyridinium Methanesulfonate). In some embodiments, the second harmonic-active moiety (such as, a label) is bound to the agent A by one or more amine groups on the surface of the agent A. In some embodiments, said one or more amine groups are native amine groups. In some embodiments, said one or more amine groups are engineered amine groups. In some embodiments of any of the embodiments provided herein, the second harmonic-active moiety (such as, a label) is PyMPO-succinimidyl ester. In some embodiments, the second harmonic-active moiety (such as, a label) is an unnatural amino acid. In some embodiments of any of the embodiments provided herein, the unnatural amino acid is Aladan. In some embodiments, the target protein is a G protein-coupled receptor, a steroid hormone receptor, or a tyrosine kinase receptor. In some embodiments of any of the embodiments provided herein, the interface is selected from the group consisting of: a glass surface, a polyethylene glycol surface, a supported lipid bilayer surface, a lipid analog bilayer surface, a plastic surface, a metal surface, a latex surface, a rubber surface, a ceramic surface, a polymeric surface, a polypropylene surface, a polyvinylidene difluoride surface, a polyethylene surface. In some embodiments, the surface is derivatized with oligo-PEG molecules or lipids. In some embodiments, wherein the oligo-PEG molecules or lipids are Ni-NTA-bearing oligo-PEG molecules or Ni-NTA-bearing lipids. In some embodiments, the surface is a supported lipid bilayer or a lipid analog bilayer. In some embodiments of any of the embodiments provided herein, the target protein comprises an affinity tag. In some embodiments of any of the embodiments provided herein, the agent A or the agent B is a small molecule chemical compound, an antibody, a non-antibody polypeptide, a carbohydrate, an inhibitory nucleic acid, or any combination thereof.

The invention further provides methods of determining specificity of a binding interaction between a target biomolecule and a candidate binding partner comprising (a) labeling the target biomolecule at a first site with a first second harmonic-active moiety; contacting the target biomolecule with the candidate binding partner; and detecting a first detectable signal upon binding between the target biomolecule and the candidate binding partner; (b) labeling the target biomolecule at a second site with a second second harmonic-active moiety; contacting the target biomolecule with the candidate binding partner; and detecting a second detectable signal upon binding between the target biomolecule and the candidate binding partner. A difference (e.g., 1%, 2%, 3%, 4%, 5% above noise level) between the first detectable signal and the second detectable signal indicates a specific binding interaction between the target biomolecule and the candidate binding partner. Optionally, the detectable signal is generated by the second harmonic-active moiety using a surface selective technique. Optionally, the surface selective technique is second harmonic generation or sum frequency generation.

The invention further provides methods of screening a library of drug candidates targeting a target biomolecule, comprising (a) labeling the target biomolecule at a first site with a first second harmonic-active moiety; contacting the target biomolecule with a first drug candidate; and detecting a first detectable signal upon binding between the target biomolecule and the candidate binding partner; (b) labeling the target biomolecule at a second site with a second second harmonic-active moiety; contacting the target biomolecule with the first drug candidate; and detecting a second detectable signal upon binding between the target biomolecule and the candidate binding partner; (c) generating a first difference between the first detectable signal and the second detectable signal; (d) labeling the target biomolecule at a first site with a first second harmonic-active moiety; contacting the target biomolecule with a second drug candidate; and detecting a third detectable signal upon binding between the target biomolecule and the candidate binding partner; (e) labeling the target biomolecule at a second site with a second second harmonic-active moiety; contacting the target biomolecule with the second drug candidate; and detecting a fourth detectable signal upon binding between the target biomolecule and the candidate binding partner; (f) generating a second difference between the third detectable signal and the fourth detectable signal; (g) selecting a drug based on the first difference and the second difference. Optionally, the detectable signal is generated by the second harmonic-active moiety using a surface selective technique. Optionally, the surface selective technique is second harmonic generation or sum frequency generation. Optionally, the methods further comprising screening the selected drug in an animal.

The detectable signal can be a change of a normalized second harmonic generation intensity. The target biomolecule can be a protein, a DNA, a RNA or an oligosaccharide. Optionally, the candidate binding partner is an allosteric modulator.

The invention further provides methods of measuring conformational change at a functionally relevant site in a target protein, comprising (a) pre-incubating the target protein with a natural or synthetic ligand that is known to bind to the protein's active site; (b) contacting the target protein with a candidate allosteric binding partner; and (c) measuring conformational change at a functionally relevant site in the target protein using a surface selective technique. Optionally, the functionally relevant site is a site that makes direct structural contact with a binding partner. Optionally, the functionally relevant site is a site that makes indirect structural contact with a binding partner. Optionally, the functionally relevant site is a site that non-structurally affects binding of and/or modulates a binding molecule. Optionally, the functionally relevant site is labeled with a second harmonic active moiety.

DETAILED DESCRIPTION

The present invention discloses, inter alia, methods for labeling a target protein with an SHG-active moiety, label, or probe for detection by second harmonic or sum-frequency generation in order to identify agents which bind to an allosteric site on the target protein thereby altering its structural conformation.

The aim of structure-based drug screening and basic studies of the mechanism of biological molecules requires a tool that can measure structure and structural change of biological molecules as they bind to ligands, drugs, or other binding partners. Present techniques for determining structural change are mainly confined to NMR (Nuclear Magnetic Resonance) and X-ray crystallography. Neither of these techniques is suitable for measuring structural change in real time. Moreover, they are time- and labor-intensive and unsuitable for wide scale use in drug screening. Furthermore, there are many proteins that are difficult to crystallize (e.g., membrane proteins) and thus many whose structures have not been determined.

Figure 1:
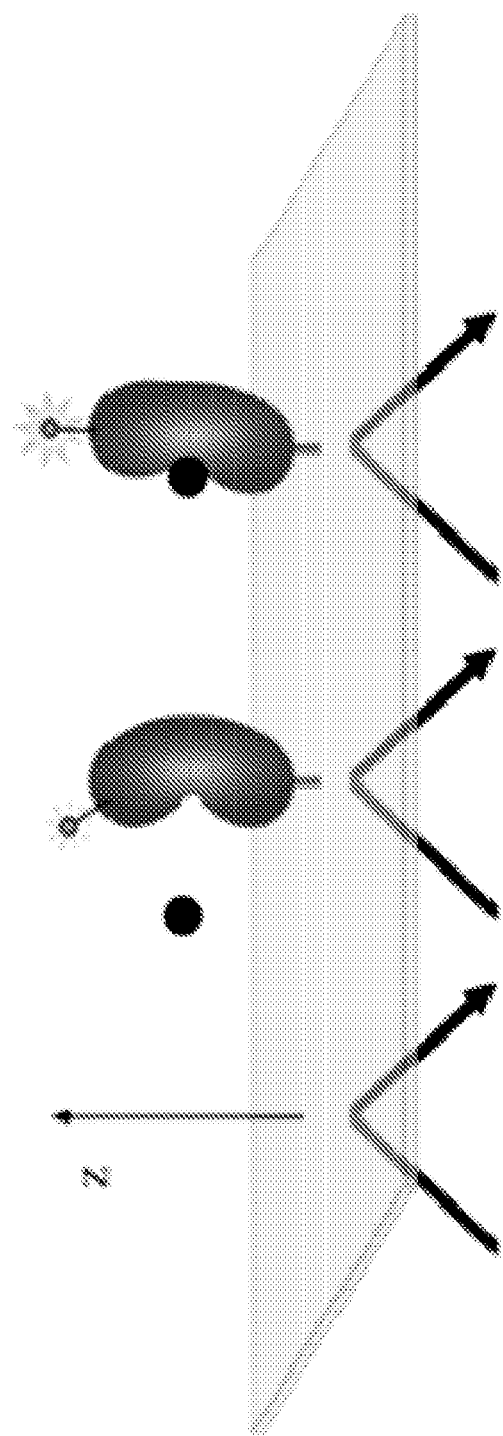
FIG. 1 depicts a schematic of the detection process for detecting conformational changes in proteins. Incident red light strikes the surface and through total internal reflection creates an evanescent wave polarized normal to the plane of the surface and traveling just a short distance from the surface (left). Labeled protein bound to surface with baseline signal dependent on the position of the dye relative to this normal (center). A conformational change that brings the label towards the normal of the evanescent wave results in a signal increase (left).
Figure 2:
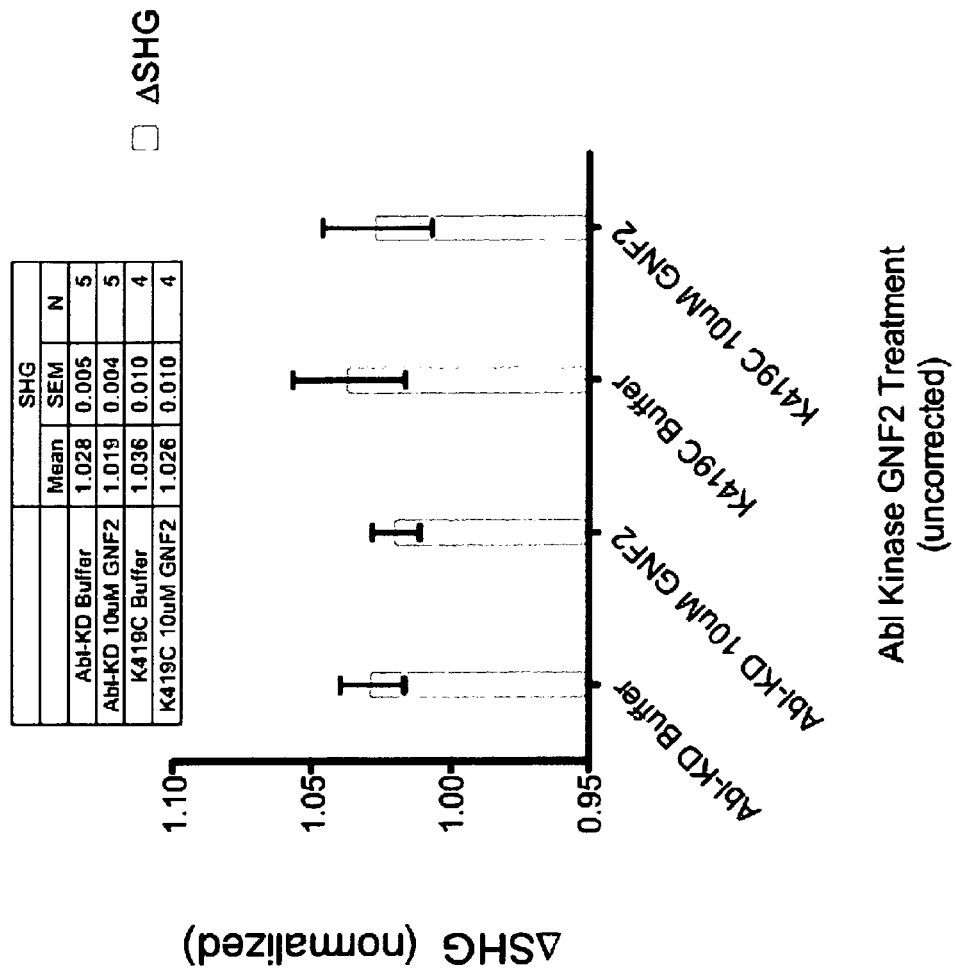
FIG. 2 depicts the results of an experiment utilizing SHG technology to measure the conformation change induced in wildtype and a K419C mutant Abl kinase upon interaction with GNF2, a known allosteric binder.

Second harmonic generation (SHG) is highly sensitive to structural shifts of an SHG-active dye probe attached to a protein. A protein of interest is labeled covalently at amine or sulfhydryl sites (e.g., lysine or cysteine residues) with an SHG-active dye probe. SHG-active dye probes are often fluorescent; the key components are the requirement of a large difference dipole moment and a non-centrosymmetric structure. SHG measurements are made by binding the labeled protein to a surface and exposing it to pulsed red light from an ultrafast laser. Under illumination, the dye probe converts a small portion of the incident red light into blue light, which is the "second harmonic" signal. This phenomenon, which does not involve absorption of light but rather relies on a mechanism similar to reflection, occurs only if there is a net, average orientation of labels; labeled molecules randomly oriented in solution produce no second harmonic light (FIG. 1). Theoretically, a population of protein in which half of the labels point toward the surface and the other half point away from it, along the same axis, would produce no second harmonic light. In practice, there is always a net, average orientation. When the average orientation of the labels shifts due to ligand binding and concomitant conformational change, the intensity of the second harmonic light changes, which is the basis of SHG's ability to detect conformational changes.

The present invention uses second harmonic generation techniques to screen for and identify allosteric modulators of target proteins. The inventors have discovered, inter alia, that pre-incubating a target protein with an agent or ligand known to bind to the target protein's active site or isolating a protein with a natural ligand bound to its active site prior to SHG screening of candidate allosteric modulators increases the probability that target protein conformational changes detected by SHG are due to the interaction of the candidate modulators at allosteric sites on the target protein, rather than the active site. The methods of the present application, therefore, represent an improvement over what has previously been practiced in the art, in that identification of allosteric modulators of protein conformation and behavior using the instantly described methods can be performed as high-throughput assays and in real time, in contrast to traditional methods which often require long periods of time to obtain results and, at best, provide only a snapshot of a protein's conformational dynamics upon binding to a ligand.

I. General Techniques

The practice of the present invention will employ, unless otherwise indicated, conventional techniques of molecular biology (including recombinant techniques), microbiology, cell biology, biochemistry, nonlinear optics detection and measurement and immunology, which are within the skill of the art. Such techniques are explained fully in the literature, "*Molecular Cloning: A Laboratory Manual*", second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., *Dictionary of Microbiology and Molecular Biology* 2nd ed., J. Wiley & Sons (New York, N.Y. 1994), March, "*Advanced Organic Chemistry Reactions, Mechanisms and Structure*" 4th ed., John Wiley & Sons (New York, N.Y. 1992), "Bioconjugate Techniques", Elsevier, (G. T. Hermanson 2008), "Second-order nonlinear optical effects at surfaces and interfaces", in Nonlinear Surface Electromagnetic Phenomena, Elsevier (Eds. H. Ponath and G. I. Stegeman, 1991) and "*Neuronal Calcium Sensor Proteins*," NOVA Publishers, (Philippov & Koch, eds., 2006) provide one skilled in the art with a general guide to many of the terms used in the present application.

II. Definitions

As used herein "second harmonic" refers to a frequency of light that is twice the frequency of a fundamental beam of light.

As used herein, a molecule or material phase is "centrosymmetric" if there exists a point in space (the "center" or "inversion center") through which an inversion (x,y,z)->>(−x,−y,−z) of all atoms is performed that leaves the molecule or material unchanged. A non-centrosymmetric molecule or material lacks this center of inversion. For example, if the molecule is of uniform composition and spherical or cubic in shape, it is centrosymmetric. Centrosymmetric molecules or materials have no nonlinear susceptibility or hyperpolarizability, necessary for second harmonic, sum frequency and difference frequency generation.

As used herein, "surface-selective" refers to a non-linear optical technique such as second harmonic generation or sum/difference frequency generation or other surface-specific technique known in the art.

As used herein, "sum frequency generation" (SFG) is a nonlinear, optical technique whereby light at one frequency ($\Omega_1$) is mixed with light at another frequency ($\Omega_2$) to yield a response at the sum frequency ($\Omega_1 + \Omega_2$) (Shen, 1984, 1989). For example, SFG is particularly useful for the detection of molecules at surfaces through their characteristic vibrational transitions and, in this case, is essentially a surface-selective infrared spectroscopy with $\Omega_1$ and $\Omega_2$ at visible and infrared frequencies. When the terms "SHG" or "second harmonic generation" are used herein, it is understood that SFG and "sum frequency generation" can substitute and be used in place of SHG with methods well known to one skilled in the art.

A "nonlinear active moiety," as used herein, is a substance which possesses a hyperpolarizability.

"Second harmonic-active moiety" or "second harmonic-active moiety," as used herein, refers to a nonlinear-active moiety, particle or molecule which can be attached (covalently or non-covalently) to a molecule (e.g., a protein, such as an enzyme), particle or phase (e.g., lipid bilayer) in order to render it more nonlinear optical active.

"Allosteric", "allosteric modulator", or "allosteric candidate" as used herein, refers to a molecule, moiety or substance which binds predominantly to a site other than the active site and causes conformational change as determined by SHG or SFG, and thus exert their effect via an allosteric mechanism of action.

"Active site" or "active binding site," as used herein, refers to a region of a target protein that, as a result of its shape and charge potential, favorably interacts or associates with another agent (including, without limitation, a ligand, a protein, polypeptide, peptide, nucleic acid, including DNA or RNA, molecule, compound, antibiotic or drug, molecule, moiety, substrate, product, analog, or inhibitor,) via various covalent and/or non-covalent binding forces and where function of the protein is performed such as, but not limited to, catalysis, signaling, and/or effector activation.

"Hyperpolarizability" or "Nonlinear Susceptibility" as used herein refer to the properties of a molecule, particle, interface, or phase which allow for generation of nonlinear light. The terms "hyperpolarizability," "second-order nonlinear polarizability," and "nonlinear susceptibility" are sometimes used interchangeably.

As referred to herein, sites that participate in a binding partner event which are "functionally relevant", as defined herein, includes any sites which make direct or indirect structural contact with the binding partner (e.g., effector molecule) as determined by a structural technique such as X-ray crystallography, NMR or SHG. Direct structural contact is defined as any residue, some portion of which is within 2 nm of some portion of the binding partner molecule. Indirect structural contact is defined as any residue, some part of which changes its orientation, conformation or relative coordinates upon binding of binding partner (e.g., effector molecule), or a binding partner mimic or analog, as seen by a structural technique such as X-ray, NMR or SHG, relative to its orientation, conformation or relative coordinates in the absence of the binding partner, mimic or analog. The term "functionally relevant" also includes residues which are known to be important in the binding or the modulation (e.g., activation, inhibition, regulation, and so on) of the binding molecule by a non-structural means (e.g., mutagenesis or biochemical data which shows that particular residues are important for binding or modulation of the binding partner).

The term "ligand", as defined herein includes any molecule that binds to another molecule, such as, but not limited to, one protein binding to another, a carbohydrate binding to a protein, or a small molecule binding to a protein.

As used herein, "nonlinear" refers to optical techniques capable of transforming the frequency of an incident light beam (a.k.a., the fundamental). The nonlinear beams are the higher order frequency beams which result from such a transformation, e.g. a second harmonic. In second harmonic, sum frequency or difference frequency generation, the nonlinear beams are generated coherently. In second harmonic generation (SHG), two photons of the fundamental beam are virtually scattered by the interface to produce one photon of the second harmonic. Also referred to herein as "nonlinear optical" or "surface-selective nonlinear."

The terms "nonlinear active" or "nonlinearly active" as used herein also refer to the general property of the ability of molecules, particles, an interface or a phase, to generate nonlinear optical radiation when driven by incident radiation beam or beams.

When referring herein to nonlinear optical methods, "detection" or "detecting" refers to those techniques by which the properties of surface-selective nonlinear optical radiation can be used to detect, measure or correlate properties of probe-target interactions (such as the interaction between a protein and a candidate modulator compound), or effects of the interactions, with properties of the nonlinear optical light (e.g., intensity, wavelength, polarization or other property common to electromagnetic radiation).

As used herein, the term "conformational change" refers to the alteration of a biological species' (for example, a protein, such as an enzyme) structural conformation.

As used herein, the term "protein" includes polypeptides, peptides, fragments of polypeptides, and fusion polypeptides.

As used herein, the term "modulator" refers to any substance (e.g., small molecule compound, peptide, protein, etc.) which alters the conformation of a protein as detected by SHG.

As used herein, an "interface" is a region which generates a nonlinear optical signal or the region near a surface in which there are second harmonic-active moiety-labeled targets possessing a net orientation. An interface can also be composed of two surfaces, a surface in contact with a different medium (e.g., a glass surface in contact with an aqueous solution, a cell surface in contact with a buffer), or the region near the contact between two media of different physical or chemical properties.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. Compositions

A. Target Proteins for Use in the Disclosed Methods

The target protein for use in any of the methods described herein may be a naturally occurring substance, or a subunit or domain thereof, from any natural source, including a virus, a microorganism (including bacterial, fungi, algae, and protozoa), an invertebrate (including insects and worms), the normal or pathological cells of an animal, a vertebrate (such as, a mammal, bird or fish and, among mammals, for example, humans, apes, monkeys, cows, pigs, goats, llamas, sheep, rats, mice, rabbits, guinea pigs, cats and dogs), or the normal or pathological cells of a plant. The target proteins may alternatively be a non-naturally occurring protein that has been created in vitro or modified such as by a mutation, a chimeric protein, or an artificial protein. The target protein may be a glyco-, lipo-, phospho-, or metalloprotein. It may be a nuclear, cytoplasmic, membrane-associated, or a secreted protein. The target protein does not need to be a single macromolecule. For example, the target protein may be a homo or hetero-multimer (such as, but not limited to, a dimer, a trimer, or a tetramer) of macromolecules. Additionally, the target protein may require one or more ligands for carrying out physiological functions, such as other proteins, oligo- or polypeptides, nucleic acids, carbohydrates, lipids, or small organic or inorganic molecules or ions. Additional examples include cofactors, ribosomes, polysomes, and chromatin.

The biological activity of the target protein for use in any of the methods disclosed herein is not limited to a specific activity such as a receptor or an enzymatic activity. Non limiting examples of target proteins include nuclear receptors, orphan nuclear receptor, tyrosine kinase receptors, endothelin, erythropoietin receptor, FAS ligand receptor, protein kinases (e.g., protein kinase C, tyrosine kinases, serine kinases, threonine kinases, nucleotide kinases, or polynucleotide kinases), protein phosphatases (serine/threonine phosphatases, tyrosine phosphatases, nucleotide phosphatases, acid phosphatases, alkaline phosphatases, or pyrophosphatases), cell cycle regulators (cyclin cdk2, CDC2, CDC25, P53, RB), GTPases, Rac, Rho, Rab, Ras, endoproteases, exoproteases, metalloproteases, serine proteases, cysteine proteases, nucleases, polymerases, reverse transcriptases, integrases, ion channels, chaperonins (i.e. heat shock proteins), deaminases, nucleases (i.e. deoxyribonuclease, ribonucleases, endonucleases, exonucleases), telomerases, primases, helicases, dehydrogenases, transferases (peptidyl transferase, transaminase, glycosyltransferases, ribosyltransferases, acetyl transferases, guanylyltransferases, or methyltransferases), hydrolases, carboxylases, isomerases, glycosidases, deaminases, lipases, esterases, sulfatases, cellulases, lyases, reductases ligases or processing enzymes of the cellular ubiquitination pathway (such as E1, E2, or E3 enzymes or deubiquitinases). In some embodiments, the target proteins for use in any of the methods disclosed herein may be structural and non-structural proteins selected among viral proteins, bacterial proteins, vegetal proteins, animal proteins and human proteins. In some embodiments, the target protein can be a viral protein, such as, but not limited to, influenza virus, a hepatitis A virus, a hepatitis B virus, a hepatitis C virus, a human immunodeficiency virus, an avian influenza virus, an Ebola virus, a SARS virus, a Hantavirus, or an eastern equine encephalitis virus.

In some aspects of any of the methods provided herein, the target protein is a receptor. The term "receptor" includes both surface and intracellular receptors. In some embodiments, the target protein is a nuclear receptor. Nuclear receptors are a family of ligand-activated transcriptional activators. These receptors are organized into distinct domains for ligand binding, dimerization, transactivation, and DNA binding. The steroid receptor family is a large family composed of receptors for glucocorticoids, mineralocorticoids, androgens, progestins, and estrogens. Receptor activation occurs upon ligand binding, which induces conformational changes allowing receptor dimerization and binding of co-activating proteins. These co-activators, in turn, facilitate the binding of the receptors to DNA and subsequent transcriptional activation of target genes. In addition to the recruitment of co-activating proteins, the binding of ligand is also believed to place the receptor in a conformation that either displaces or prevents the binding of proteins that serve as co-repressors of receptor function. If the ligand is a pharmacological agonist, the new conformation is one which interacts with other components of a biological signal transduction pathway, e.g.; transcription factors, to elicit a biological response in the target tissue. If the ligand is a pharmacological antagonist, the new conformation is one in which the receptor cannot be activated by one or more agonists which otherwise could activate that receptor. A non-exhaustive list of NRs is described in International Patent Application Publication No. 2006/046134, this disclosure of which is incorporated by reference herein (see pages 14 and 15, and FIG. 1). In some embodiments, the NRs for use in any of the methods disclosed herein can be selected from among an estrogen receptor, an androgen receptor, a glucocorticoid receptor, a retinoic acid receptor alpha (RARG), a retinoic X receptor (RXR), a peroxisome proliferators-activated receptor (PPARs), a liver X receptor alpha (LXRG) or a progesterone receptor.

In some aspects, the target protein for use in any of the methods described herein is a G protein-coupled receptor (also known as seven-transmembrane domain receptors). A "G-protein coupled receptor (GPCR)" refers to any member of a superfamily of receptors that mediates signal transduction by coupling with a G protein. GPCRs comprise a large family of transmembrane receptor proteins (representing about 5% of the total genome of humans) that bind to molecules present in the extracellular environment and are capable of triggering signal transduction cascades within the cell and, ultimately, cellular responses. GPCRs are found only in eukaryotes, including yeast, choanoflagellates, and animals. The molecules that bind and activate these receptors include, but are not limited to, light-sensitive compounds, odors, pheromones, hormones, and neurotransmitters, and vary in size from small molecules to peptides to large proteins. One example of a class of GPCR which influences cytosolic calcium levels works through the Gq type of G proteins, which activate a phospholipase C (PLC) pathway, resulting in the hydrolysis of phosphoinositides to generate two classes of different second messengers, namely, diacylglycerol and inositol phosphates. Diacylglycerol, in turn, activates certain protein kinase Cs (PKCs) while inositol phosphates (such as, but not limited to, IP3) stimulate the mobilization of calcium from intracellular stores such as the endoplasmic reticulum, the sarcoplasmic reticulum (for muscle cells), and/or the mitochondria. GPCRs are found only in eukaryotes, including yeast, choanoflagellates, and animals. The molecules that bind and activate these receptors include, but are not limited to, light-sensitive compounds, odors, pheromones, hormones, and neurotransmitters, and vary in size from small molecules to peptides to large proteins.

GPCRs for use in the methods disclosed herein include, but are not limited to, $G_q$ protein or $G_{q/11}$, alpha-1 adrenegic receptors ($\alpha$1-AR), urotensin (UT) receptors, 5-HT2 and 5-HT6 serotonin receptors, hypocretic (orexin) receptors, histamine HI receptors, bradykinin B1 and B2 receptors, bombesin BB2 receptors, P2Y purinergic receptors, acetylcholine receptors (e.g., M1, M3 and M5), mGluR5 glutamate receptors, vasopressin V2 and VI receptors, angiotensin AGTR1 receptors, cholecystokinin CCKAR and CCKBR receptors, endothelin ENDRA receptors, ghrelin GHSR1a receptors, melatonin MTNR1A receptors, neurotensin NTSR1 receptors, platelet-activating factor PTAFR receptors, luteinizing hormone receptors (LHRs), follicle stimulating hormone receptors (FSHRs), gonadotrophic releasing hormone receptors (GnRHRs), and prolactin releasing peptide receptor PRLHR receptors. In some embodiments, the GPCR is endogenously expressed in the cell expressing the calcium sensor protein. In other embodiments, the GPCR is heterologously expressed in the cell expressing the calcium sensor protein.

In other aspects, the target protein for use in the methods of the present invention can be a kinase. A kinase is a type of enzyme that transfers phosphate groups from high-energy donor molecules, such as ATP, to specific substrates, a process referred to as phosphorylation. One of the largest groups of kinases are protein kinases, which act on and modify the activity of specific proteins. Kinases are used extensively to transmit signals and control complex processes in cells. More than five hundred different kinases have been identified in humans. Their enormous diversity, as well as their role in signaling, makes them an object of study particularly with regard to disease states characterized by aberrant kinase expression or regulation.

Protein kinases contain a large flexible loop, called the activation loop or A-loop, whose conformation is believed to regulate kinase activity. In many kinases, the conformation of the A-loop is controlled by the phosphorylation of specific residues within this region (Johnson 1996). The activation loop generally begins with a conserved AspPheGly sequence and ends at a conserved AlaProGlu. In structures of inactive kinases, this loop often blocks either the substrate or ATP binding sites (Hubbard 1994; Mohammadi 1996; and McTigue 1999). Tyrosine kinases usually have one or two tyrosines in the loop, MAPK kinases have a T[DE]Y motif, which is phosphorylated on both T and Y, while most other kinases have a threonine within the loop.

The target proteins for use in the methods of the invention are broadly applicable to any protein kinase. These can include protein tyrosine kinases and protein serine kinases. Non-limiting examples of protein tyrosine kinases are pp60c-src, p56lck, ZAP kinase, platelet derived growth factor receptor tyrosine kinase, Bcr-Abl, VEGF (vascular endothelial growth factor) receptor tyrosine kinase, and epidermal growth factor receptor tyrosine kinase, and epidermal growth factor receptor-like tyrosine kinases. Non-limiting examples of serine protein kinases applicable for use in the present invention include MAP (mitogen activated protein) kinase, protein kinase C, protein kinase A, Akt, and CDK (cyclin dependent protein kinase). In mammalian biology, protein kinases belonging to the mitogen activated protein kinase (MAPK) family are inappropriately activated in a variety of proliferative cell diseases (such as, for example, cancers) associated with the mutation of ras genes and deregulation of growth factor receptors (Magnuson et al., *Seminars in Cancer Biology*, 5:247-252 (1994)). MAP kinases are known in the art and a partial non-limiting list of such kinases includes abl, Aurora-A, Aurora-B, Aurora-C, ATK, bcr-abl, Blk, Brk, Btk, c-Kit, c-Met, c-Src, CDK1, CDK2, CDK4, CDK6, cRafl, CSF1R, CSK, EGFR, ErbB2, ErbB3, ErbB4, ERK, Fak, fes, FGFR1, FGFR2, FGFR3, FGFR4, FGFR5, Fgr, FLK-4, Flt-1, Fms, Fps, Frk, Fyn, Hck, IGF-1R, INS-R, Jak, KDR, Lck, Lyn, MEK, p38, PDGFR, PIK, PKC, PYK2, Ros, Tie1, Tie2, Trk, Yes and Zap70. In some embodiments of the methods described herein, the kinase is abl kinase.

With respect to kinases, several types of compounds are known to modulate the function of kinases. For example, type I kinase inhibitors recognize the active conformation of a kinase. They bind to the ATP-binding site by presenting one to three hydrogen bonds which mimic the hydrogen bonds normally formed by ATP. Without being bound to theory, it is believed that, in contrast to type I kinase inhibitors, type II kinase inhibitors recognize the inactive conformation of a kinase and can indirectly compete with ATP by occupying the hydrophobic pocket directly adjacent to the ATP-binding site. This hydrophobic pocket is created by the unique DFG-out conformation of the activation loop. While this is not necessary for functionality, some type II inhibitors are able to form a hydrogen bond directly to the ATP-binding site (Gotink & Verheul, *Angiogenesis*, 2010, 13(1): 1-14). Type III kinase inhibitors, on the other hand, are non-ATP competitive kinase inhibitors which modulate kinase activity by binding to sites other than the activation loop (i.e. by binding to allosteric sites on the kinase). Due to the fact that Type III compounds bind to less-conserved sites on kinases, they are highly selective and are of increasing interest to the research and drug discovery communities.

Also contemplated for use within the scope of the methods of the present invention are mutant forms of target proteins. As used herein, a "mutation" includes an amino acid residue deletion, an amino acid residue insertion, and/or an amino acid residue substitution of at least one amino acid residue in a defined primary amino acid sequence, such as a primary amino acid sequence of a target protein. An amino acid "substitution" means that at least one amino acid component of a defined primary amino acid sequence is replaced with another amino acid (for example, a cysteine residue or a lysine residue). Methods for engineering a mutation or substitution into the primary amino acid sequence of a target protein are well known in the art via standard techniques. The target proteins for use in the methods described herein may include conservative substitutions. Conservative substitutions are shown in the "Table of Amino Acid Substitutions" below under the heading of "preferred substitutions." If substitutions result in a change in biological activity, then more substantial changes, denominated "exemplary substitutions" in the table below, or as further described below in reference to amino acid classes, may be introduced.

| Potential amino acid substitutions | | |
| --- | --- | --- |
| Original Residue | Exemplary Substitutions | Preferred Substitutions |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of target proteins are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Non-conservative substitutions will entail exchanging a member of one of these classes for another class.

In further embodiments, mutant target proteins for use in any of the methods disclosed herein may comprise one or more non-naturally occurring or modified amino acids. A "non-naturally occurring amino acid residue" refers to a residue, other than those naturally occurring amino acid residues listed above, which is able to covalently bind adjacent amino acid residues(s) in a polypeptide chain. Non-natural amino acids include, but are not limited to homo-lysine, homo-arginine, homo-serine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, citrulline, pentylglycine, pipecolic acid and thioproline. Modified amino acids include natural and non-natural amino acids which are chemically blocked, reversibly or irreversibly, or modified on their N-terminal amino group or their side chain groups, as for example, N-methylated D and L amino acids, side chain functional groups that are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide and a modified amino acid of alanine. Additional non-natural and modified amino acids, and methods of incorporating them into proteins and peptides, are known in the art (see, e.g., Sandberg et al., (1998) *J. Med. Chem.* 41: 2481-91; Xie and Schultz (2005) *Curr. Opin. Chem. Biol.* 9: 548-554; Hodgson and Sanderson (2004) *Chem. Soc. Rev.* 33: 422-430).

In some embodiments, mutant target proteins for use in the methods described herein can be isolated from cells (such as a cancer cell) by an appropriate purification scheme using standard protein purification techniques. In another embodiment, mutant target proteins for use in the instantly described methods are produced by recombinant DNA techniques. Alternative to recombinant expression, mutant target proteins for use in the methods described herein can be synthesized chemically using standard peptide synthesis techniques.

B. Agents for Use in Methods to Identify Allosteric Modulators of Target Proteins In some aspects, the agents for use in the methods described herein can be unknown candidate allosteric modulators of a target protein. The agents for use in the methods described herein can be any of a small molecule chemical compound, an antibody, a non-antibody polypeptide, a carbohydrate, an inhibitory nucleic acid, or any combination thereof. In some embodiments, the agent is an antibody (such as a humanized antibody) or a fragment thereof. Alternatively, the agent may be a small molecule compound. In other embodiments, the agent can be a non-antibody polypeptide (such as an isolated non-antibody polypeptide). In some embodiments, agent is a peptide (for example, an isolated peptide).

1. Non-Antibody Binding Polypeptides

In some aspects, the agents for use in the methods described herein are non-antibody binding polypeptides. Binding polypeptides are polypeptides that bind, preferably specifically, to a target protein such as any of the target proteins described herein. Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding, preferably specifically, to a wild type or mutant target protein. Binding polypeptides may be identified without undue experimentation using well known techniques. In this regard, it is noted that techniques for screening polypeptide libraries for binding polypeptides that are capable of binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO 84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth.*, 102:259-274 (1987); Schoofs et al., *J. Immunol.*, 140:611-616 (1988), Cwirla, S. E. et al., (1990) *Proc. Natl. Acad. Sci. USA*, 87:6378; Lowman, H. B. et al., (1991) *Biochemistry*, 30:10832; Clackson, T. et al., (1991) *Nature*, 352: 624; Marks, J. D. et al., (1991), *J Mol. Biol.*, 222:581; Kang, A. S. et al., (1991) *Proc. Natl. Acad. Sci. USA*, 88:8363, and Smith, G. P. (1991) *Current Opin. Biotechnol.*, 2:668).

Bacteriophage (phage) display is one well known technique which allows one to screen large polypeptide libraries to identify member(s) of those libraries which are capable of binding to a target polypeptide, such as a wild type or mutant target protein for use in the methods disclosed herein. Phage display is a technique by which variant polypeptides are displayed as fusion proteins to the coat protein on the surface of bacteriophage particles (Scott, J. K. and Smith, G. P. (1990) *Science*, 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al., (1990) *Proc. Natl. Acad. Sci. USA*, 87:6378) or protein (Lowman, H. B. et al., (1991) *Biochemistry*, 30:10832; Clackson, T. et al., (1991) *Nature*, 352: 624; Marks, J. D. et al., (1991), *J. Mol. Biol.*, 222:581; Kang, A. S. et al., (1991) *Proc. Natl. Acad. Sci. USA*, 88:8363) libraries on phage have been used for screening millions of polypeptides or oligopeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. See U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., *Gene*, 215: 439 (1998); Zhu et al., Cancer *Research*, 58(15): 3209-3214 (1998); Jiang et al., *Infection & Immunity*, 65(11): 4770-4777 (1997); Ren et al., *Gene*, 195(2):303-311 (1997); Ren, *Protein Sci.*, 5: 1833 (1996); Efimov et al., *Virus Genes*, 10: 173 (1995)) and T7 phage display systems (Smith & Scott, *Methods in Enzymology*, 217: 228-257 (1993); U.S. Pat. No. 5,766,905) are also known.

Additional improvements enhance the ability of display systems to screen peptide libraries for binding to selected target molecules and to display functional proteins with the potential of screening these proteins for desired properties.

Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al., (1998) *Mol Biotech.*, 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

The binding polypeptides can be modified to enhance their inhibitory effect (including, for example, enhanced affinity, improved pharmacokinetic properties such as half-life, stability, and clearance rate, reduced toxicity, etc.). Such modifications include, for example, glycosylation, pegylation, substitution with non-naturally occurring but functionally equivalent amino acid, linking groups, etc.

2. Small Molecules

In some aspects, the agents for use in the methods described herein are small molecule chemical compounds. Small molecules are preferably organic molecules other than binding polypeptides or antibodies as defined herein that bind, preferably specifically, to a wild type or mutant target protein. Organic small molecules may be identified and chemically synthesized using known methodology (see, e.g., PCT Publication Nos. WO00/00823 and WO00/39585). Organic small molecules are usually less than about 2000 Daltons in size, alternatively less than about 1500, 750, 500, 250 or 200 Daltons in size, wherein such organic small molecules that are capable of binding, preferably specifically, to a wild type or mutant target protein may be identified without undue experimentation using well known techniques. In this regard, it is noted that techniques for screening organic small molecule libraries for molecules that are capable of binding to a polypeptide target are well known in the art (see, e.g., PCT Publication Nos. WO00/00823 and WO00/39585). Organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

In some aspects, the small molecule chemical compound is a component of a combinatorial chemical library. Combinatorial chemical libraries are a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of binding an acceptor molecule (such as a c-met protein) or mediating a biological activity of interest (such as, but not limited to, inhibition of cellular proliferation).

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. In some embodiments, the small molecules are less than about 2000 Daltons in size, alternatively less than about 1500, 750, 500, 250 or 200 Daltons in size.

The small molecule agents described in any of the aspects herein can be derived from any type of chemical reaction that can be carried out on a solid support. Such chemical reactions include, but are not limited to, 2+2 cycloadditions including trapping of butadiene; [2+3] cycloadditions including synthesis of isoxazolines, furans and modified peptides; acetal formation including immobilization of diols, aldehydes and ketones; aldol condensation including derivatization of aldehydes, synthesis of propanediols; benzoin condensation including derivatization of aldehydes; cyclocondensations including benzodiazepines and hydantoins, thiazolidines, turn mimetics, porphyrins, phthalocyanines; Dieckmann cyclization including cyclization of diesters; Diels-Alder reaction including derivatization of acrylic acid; Electrophilic addition including addition of alcohols to alkenes; Grignard reaction including derivatization of aldehydes; Heck reaction including synthesis of disubstituted alkenes; Henry reaction including synthesis of nitrile oxides in situ (see 2+3 cycloaddition); catalytic hydrogenation including synthesis of pheromones and peptides (hydrogenation of alkenes); Michael reaction including synthesis of sulfanyl ketones, bicyclo[2.2.2]octanes; Mitsunobu reaction including synthesis of aryl ethers, peptidyl phosphonates and thioethers; nucleophilic aromatic substitutions including synthesis of quinolones; oxidation including synthesis of aldehydes and ketones; Pausen-Khand cycloaddition including cyclization of norbornadiene with pentynol; photochemical cyclization including synthesis of helicenes; reactions with organometallic compounds including derivatization of aldehydes and acyl chlorides; reduction with complex hydrides and tin compounds including reduction of carbonyl, carboxylic acids, esters and nitro groups; Soai reaction including reduction of carboxyl groups; Stille reactions including synthesis of biphenyl derivatives; Stork reaction including synthesis of substituted cyclohexanones; reductive amination including synthesis of quinolones; Suzuki reaction including synthesis of phenylacetic acid derivatives; and Wittig-Horner reactions including reactions of aldehydes, pheromones, and sulfanyl ketones.

References disclosing the synthesis of chemical libraries as well as the deconvolution of the individual compounds of those libraries onto individual solid phase supports, can be found in U.S. Patent Application No. 2009/0032592; Needels et al., (1993), *Proc. Natl. Acad. Sci. USA* 90: 10700-10704; and WO 97/15390.

3. Antibodies

In some aspects, the agents for use in the methods described herein are antibodies. Antibodies are proteins that bind, preferably specifically, to a target protein. Variants of antibodies can be made based on information known in the art, without substantially affecting the activity of antibody. For example, antibody variants can have at least one amino acid residue in the antibody molecule replaced by a different residue. For antibodies, the sites of greatest interest for substitutional mutagenesis generally include the hypervariable regions, but framework region (FR) alterations are also contemplated.

For antibodies, one type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In one embodiment, the Fc region variant may display altered neonatal Fc receptor (FcRn) binding affinity. Such variant Fc regions may comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Fc region variants with reduced binding to an FcRn may comprise an amino acid modification at any one or more of amino acid positions 252, 253, 254, 255, 288, 309, 386, 388, 400, 415, 433, 435, 436, 439 or 447 of the Fc region, wherein the numbering of the residues in the Fc region is that of the EU index as in Kabat. The above-mentioned Fc region variants may, alternatively, display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat.

The Fc region variant with reduced binding to an FcR may comprise an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat.

For example, the Fc region variant may display reduced binding to an FcRI and comprise an amino acid modification at any one or more of amino acid positions 238, 265, 269, 270, 327 or 329 of the Fc region, wherein the numbering of the residues in the Fc region is that of the EU index as in Kabat.

The Fc region variant may display reduced binding to an FcRII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

The Fc region variant of interest may display reduced binding to an FcRIII and comprise an amino acid modification at one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

Fc region variants with altered (i.e. improved or diminished) C1q binding and/or Complement Dependent Cytotoxicity (CDC) are described in International Patent Application No.: WO99/51642. Such variants may comprise an amino acid substitution at one or more of amino acid positions 270, 322, 326, 327, 329, 331, 333 or 334 of the Fc region. See, also, Duncan & Winter Nature 322:738-40 (1988); U.S. Pat. Nos. 5,648,260; 5,624,821; and International Patent Application No.: WO94/29351 concerning Fc region variants.

C. Second Harmonic-Active Moieties (Such as, Labels)

In some aspects of any of the methods provided herein, the wild type or mutant target protein is labeled with a second harmonic-active moiety or label (a.k.a an SHG-moiety or SHG-label). Second harmonic-active moieties (such as, a label) can be bound, either covalently or non-covalently, to a target protein in order to render the resulting target protein susceptible to second harmonic generation and amenable to study at an interface using a surface-selective technique. The labeled target proteins may then be studied by surface-selective techniques such as second harmonic generation or sum-frequency generation. The exogenous moieties (such as, a label) can be pre-attached to the target protein, and any unbound or unreacted labels separated from the labeled entities before a measurement is made. In a one embodiment, the second harmonic-active moiety (such as, a label) is attached to the target protein in vitro. The labeling of a target protein with a second harmonic-active moiety (such as, a label) permits a direct, optical means of detecting target protein conformational changes in cases where a binding reaction (such as the binding of an agent capable of stabilizing a target protein into an active or inactive conformation) results in a change in the orientation or conformation of the label using a surface-selective nonlinear optical technique. Unlike detection with fluorescent labels, SHG-labels have the important advantage that only labeled target proteins at an interface and with a net orientation contribute to the second harmonic signal; labeled target proteins that fail to attach to the surface contribute no signal. Therefore, the signal-to-noise ratio for detecting conformational changes in SHG-labeled target protein molecules upon the binding of an agent is invariably and consistently high. In some embodiments, the target proteins are labeled with an SHG-active moiety (such as, a label) in situ (i.e., after being attached to the surface). In other embodiments, the target proteins are labeled with an SHG-active moiety (such as, a label) after being attached to a supported lipid bilayer surface or a supported lipid analog bilayer surface.

In alternate aspects of the invention, at least two distinguishable second harmonic-active moieties (such as, labels) can be used. The orientation of the attached two or more distinguishable labels would then be chosen to facilitate well defined directions of the emanating coherent nonlinear light beam. The two or more distinguishable labels can be used in assays where multiple fundamental light beams at one or more frequencies, incident with one or more polarization directions relative to the sample, are used, with the resulting emanation of at least two nonlinear light beams. In one embodiment, the second harmonic-active moiety (such as, a label) comprises a plurality of individual second harmonic-active moieties (such as, labels) which each have a nonlinear susceptibility and are bound together in a fixed and determinate orientation with respect to each other so as to increase the overall nonlinear susceptibility of the second harmonic-active moiety (such as, a label).

1. Second Harmonic-Active Dyes

In some aspects of the methods described herein, the second harmonic-active moiety (such as, a label) is a dye. The target protein can be labeled by a dye through specific labeling or non-specific labeling.

The second harmonic-active moiety can be attached to a target protein through specific labeling, e.g., via a covalent bond or a hydrogen bond. For example, the second harmonic-active moiety (such as, a label) can be covalently or non-covalently attached to an amine group, a lysine group, or a sulfhydryl group in the primary amino acid sequence of the target protein to be detected. In some embodiments, the second harmonic-active moiety (such as, a label) possesses an amine-reactive succinimidyl ester, a thiol-reactive maleimide, or an aldehyde- and/or ketone-reactive hydrazide and hydroxylamine. In some embodiments, the SFG or SHG-active dye label can be conjugated via "click chemistry" for coupling to azides. Details of click chemistry for use in conjugate formation are described in: "Synthesis and Functionalization of Biomolecules via Click Chemistry", C. Schilling et al, Chapter 15 pages 355-378 in *"Click Chemistry for Biotechnology and Materials Science"* J. Lahann (Ed), Wiley (2009).

Examples of dyes appropriate for use as second harmonic or sum frequency-active moieties (such as, a label) in the methods disclosed herein include, without limitation, maleimide labels (such as PyMPO-MALEIMIDE™ (1-(2-Maleimidylethyl)-4-(5-(4-Methoxyphenyl)Oxazol-2-yl)Pyridinium Methanesulfonate), which specifically labels proteins on cysteine residues), PyMPO-NHS (which specifically labels lysine residues), oxazole labels (such as PyMPO-succinimidyl ester which specifically labels amines), BADAN™ (6-Bromoacetyl-2-Dimethylaminonaphthalene), and ACRYLODAN™ (6-Acryloyl-2-Dimethylaminonaphthalene). In other embodiments, the labels can be coumarin-based dyes such as, but not limited to, ketocoumarin, and 3,3'-carbonyl bis (7-diethylaminocoumarin). In other embodiments, the label can be PyMPO-SE™ (1-(3-(Succinimidyloxycarbonyl) Benzyl)-4-(5-(4-Methoxyphenyl)Oxazol-2-yl)Pyridinium Bromide).

In some aspects of the instantly disclosed methods, a native amino acid residue in the primary amino acid sequence of the target protein can be mutated or substituted with another amino acid that is capable of binding to a second harmonic-active dye. As used herein, a "mutation" includes an amino acid residue deletion, an amino acid residue insertion, and/or an amino acid residue substitution of at least one amino acid residue in a defined primary amino acid sequence, such as a primary amino acid sequence of a target protein. An amino acid "substitution" means that at least one amino acid component of a defined primary amino acid sequence is replaced with another amino acid (for example, a cysteine residue or a lysine residue). Desirably, mutation or substitution of one or more amino acid residues (such as a conservative mutation or substitution) in a primary amino acid sequence does not result in substantial changes in the susceptibility of a target protein encoded by that amino acid sequence to undergo a conformational change upon binding to a ligand of that target protein or upon binding to an unknown candidate agent capable of allosterically binding a target protein.

Methods for engineering a mutation or substitution into the primary amino acid sequence of a protein such as a target protein are well known in the art via standard techniques. The target proteins described herein may include conservative substitutions. Conservative substitutions are shown in the "Table of Amino Acid Substitutions" above under the heading of "preferred substitutions."

2. Unnatural Amino Acids

In other aspects, the second harmonic-active moiety (such as, a label) may be an unnatural amino acid (UAA). In contrast to conventional labels, UAA's offer a means of labeling proteins at both buried and exposed sites. Additionally, as innate components of the protein, they can report structural changes with more sensitivity and fidelity than labels (such as dyes) attached to amino acid functional groups (such as cysteines and amines). UAAs's possess hyperpolarizability for detecting proteins using a nonlinear technique such as second harmonic generation. Therefore, these specific unnatural amino acids have also been referred to as SHAA's ("Second harmonic Amino-Acid"). Another advantage of using UAA's as probes for detection of changes in protein structural confirmation is that the detection can be carried out in vivo—that is, in live cells. For example, the methods described herein can be used to detect the conformational change exhibited by a target protein in live cells in response to binding of a candidate agent. By using an oriented protein population of target proteins relative to a surface, a highly precise map of structure or conformational change in real space and real time can be built using target proteins containing a UAA as part of its amino acid sequence. Desirably, substitution of one or more amino acid residues with a UAA in a primary amino acid sequence does not result in substantial changes in the susceptibility of a target protein encoded by that amino acid sequence to undergo a conformational change upon binding to GDP or GTP or upon hydrolysis of GTP or upon binding to an unknown candidate agent capable of binding a target protein and stabilizing it into either an inactive or active conformation.

Any hyperpolarizable UAA can be used as a second harmonic-active moiety (such as, a label) to measure conformational changes in the structure of a target protein upon binding a candidate agent in any of the methods described herein. In some embodiments, the UAA is Aladan (Cohen et al., 2002, *Science*, 296:1700; Abbyad et al., 2007, *J. Phys. Chem.*, 111: 8269, the disclosures of which are incorporated herein by reference in their entireties). In other embodiments, the UAA is Dansylalanine (Summerer et al., *Proc. Nat. Acad. Sci. U.S.A.*, 2006, 103(26): 9785-9789). In one embodiment, the unnatural amino acid is sum-frequency generation-active (SFG-active). As used herein, "sum-frequency generation-active" refers to an SH active label that possess a hyperpolarizability and is detectable by SFG. In other embodiments, the UAA is not hyperpolarizable, but possesses the appropriate chemical functional group or groups to permit it to bind to a second harmonic-active label dye, such as any of the dyes described above. In other embodiments, the UAA can include a probe with tailored vibrational properties for engineering into discreet sites within a protein to identify site-specific conformational changes by SFG. In some embodiments, probe moieties for inclusion into UAAs desirably are small enough so that they do not perturb native protein structure and can include, but are not limited to, NO, CN, SCN or $N_3$. In some embodiments, the probe moieties provide unique vibrational signatures in the spectral range of between about 1,900 and 2,300 $cm^{-1}$, which is well separated from intrinsic protein vibrations. In another embodiment, a UAA can be used to attach the target protein to a surface, such that a second harmonic-active moiety (such as, a label) possesses a net orientation with respect to the surface.

Accordingly, in some aspects, structural changes in the conformation of a target protein can be determined in real time and real space by measuring the tilt angle or absolute tilt angle of an unnatural amino acid label, or a series of such labels, engineered into the amino acid sequence in different mutants of the target protein. The probes can be incorporated at any site within the target protein or at its termini, or in any domain thereof. In some embodiments, the target protein can include a second harmonic-active label that is chemically equipped to react covalently with a UAA. For example, if the UAA incorporated into a protein is Para-acetyl-phenylalanine (pAcF), the second harmonic-active dye would have appropriate chemistry on it for bonding covalently to pAcF. In another embodiment, the incorporation of a SHAA in addition to a second UAA, the second UAA (which will in general not be second harmonic-active) allows chemically orthogonal covalent coupling of the protein in an oriented manner to a surface derivatized with appropriate chemistry for reaction with the second UAA. With a highly oriented target protein sample that is SH-active (using the two UAA's), both the baseline SHG signal and the contrast (change in signal with conformational change) can be larger in comparison to target proteins which do not utilize UAA's to produce SHG signals.

In other aspects, use of one or more UAA's in the amino acid sequence of a target protein in any of the methods disclosed herein enables the determination of the actual conformational change the target protein undergoes upon binding to a candidate allosteric modulator by determining the tilt angle of one or more labels at one or more sites within the target protein as a function of time. The three dimensional structure of the target protein can be determined by making one or more mutants of a protein each containing a SHAA probe placed in a different location (i.e., the probe orientation relative to the surface in each mutant, and therefore the side-chain orientation, can be determined for the probe in each mutant and a model of the overall three dimensional protein structure can be built using this information). Information from steric hindrance methods, statistical methods, molecular dynamics, Ramachandran plots, or energy minimization methods known to those skilled in the art can be used to further aid in determining the structure given the measured probe tilt angles. A time-resolved measurement of the tilt angle of a probe produces a motion picture of a conformational change of a protein as it occurs in real time. Because of SHG's (and SFG's) virtually instantaneous response and sensitivity, spatial orientation of a particular probe (e.g., tilt angle or absolute tilt angle relative to a surface) can be measured in real time at almost any time scale of interest.

Further information related to the use of UAA's in SHG techniques can be found in U.S. Patent Application Publication No.: 2010/0068144, the disclosure of which is incorporated herein by reference in its entirety.

D. Interfaces

In some aspects of the methods disclosed herein, the target protein is bound to a solid surface or oriented with respect to an interface such that a second harmonic-active-label bound to the target protein has a net orientation. It is this net orientation than can change upon binding a GTP or GDP, upon hydrolysis of GTP within the target protein active site, or upon binding of a candidate agent capable of stabilizing the structure of a mutant or wild type target protein into an inactive or active conformation, provided that the agent induces a conformational change in the structure of the labeled target protein. In some embodiments, the interface can be made of silica, glass, silicon, polystyrene, nylon, plastic, a metal, semiconductor or insulator surface, or any surface to which biological components can adsorb or be attached. In different embodiments, the interface can be a vapor-liquid interface, a liquid-liquid interface, a liquid-solid, or a solid-solid interface. In one embodiment, the vapor-liquid interface is an air-water interface. In one embodiment, the liquid-liquid interface is an oil-water interface. In different embodiments, the liquid-solid interface is a water-glass interface or a benzene-$SiO_2$ interface.

In some aspects, the interface can also include biological cell and liposome surfaces. The attachment or immobilization can occur through a variety of techniques well known in the art. For example, with proteins, the surface can be derivatized with aldehyde silanes for coupling to amines on surfaces of biomolecules (MacBeath and Schreiber, 2000—relevant portions of which are incorporated by reference herein). BSA-NHS (BSA-N-hydroxysuccinimide) surfaces can also be used by first attaching a molecular layer of BSA to the surface and then activating it with N,N'-disuccinimidyl carbonate. The activated lysine, aspartate or glutamate residues on the BSA react with surface amines on the proteins.

Supported phospholipid bilayers can also be used, with or without membrane proteins or other membrane associated components as, for example, in Salafsky et al., *Biochemistry*, 1996—relevant portions of which are incorporated by reference herein by reference, "*Biomembranes*", Gennis, Springer-Verlag, Kalb et al., 1992, and Brian et al., 1984, relevant portions of which are incorporated herein by reference. Supported phospholipid bilayers are well known in the art and there are numerous techniques available for their fabrication, with or without associated membrane proteins.

These supported bilayers typically must be submerged in aqueous solution to prevent their destruction when they become exposed to air. In some embodiments, the surface is a lipid analog bilayer surface.

If a solid surface is used (e.g., planar substrate, beads, etc.) it can also be derivatized via various chemical reactions to either reduce or enhance its net surface charge density to optimize the detection of target protein-candidate allosteric modulator interactions. In other embodiments, the solid surface can be a glass surface, a plastic surface, a metal surface, a latex surface, a rubber surface, a ceramic surface, a polymeric surface, a polypropylene surface, a polyvinylidene difluoride surface, a polystyrene surface, or a polyethylene surface (such as a polyethylene glycol surface). The support on which the target proteins are immobilized may be composed from a wide range of material, such as, but not limited to, biological, nonbiological, organic, inorganic, or a combination of any of these, existing as particles, strands, precipitates, gels, sheets, tubing, spheres, containers, capillaries, pads, slices, films, plates, or slides. The surface may have any convenient shape, such as, but not limited to, a disc, square, sphere, or circle. The surface can be preferably flat but may also take on a variety of alternative surface configurations. For example, the surface may contain raised or depressed regions on which a sample (such as a protein) is located. The surface preferably forms a rigid support on which the sample can be formed. The surface is also chosen to provide appropriate light-absorbing characteristics. For example, the surface may be, without limitation, a polymerized Langmuir Blodgett film, functionalized glass, Si, Ge, GaAs, GaP, $SiO_2$ $SiN_4$, modified silicon, or any one of a wide variety of gels or polymers such as (poly)tetrafhioroefhylene, (poly)vinylidenedifluoride, polyethylene glycol, polystyrene, polycarbonate, or combinations thereof. Other surface materials will be readily apparent to those of skill in the art. In one embodiment the substrate is flat glass or silica.

In some aspects, the surface can be etched using well known techniques to provide for desired surface features. For example, by way of the formation of trenches, v-grooves, mesa structures, or the like, the target proteins (such as, synthesis regions of proteins) may be more closely placed within the focus point of impinging light. The surface may also be provided with reflective "mirror" structures for maximization of emission collected therefrom. As another example, the surface can be etched to form wells.

In another aspect of the present invention, oligo-polyethylene glycol (PEG) molecules can be used for immobilizing an affinity-tagged target protein to a surface for SHG or SFG detection. In some embodiments, the PEG can be SAT(PEG4) (N-Succinimidyl S-acetyl(thiotetraethylene glycol). A pegylated interface suitable for detecting SHG signals can be prepared by coating a suitable surface, such as any of the surfaces described above, with an oligo PEG solution. In one embodiment the surface can be glass. In another embodiment, the surface can be amino-terminated silane derivatized glass. Affinity tags are common in the art and may be, for example, a histidine tag (such as a $His_6$ tag), a maltose binding protein tag, an HA tag, a biotin tag, a thiol tag, or a GST tag. In some embodiments, the affinity tag is a histidine having any of 1, 2, 3, 4, 5, 6, 7, 8, 9, 10, 11, 12, 13, 14, 15, 16, 17, 18, 19, 20, or more histidine residues. In one embodiment the oligo-PEG molecules are modified with an agent that will bind to the affinity tag expressed on the target protein. The agent can be nickel, in the case of a histidine tag, or it can be a sugar (such as maltose), an antibody, or any other molecule known in the art that is capable of binding to an affinity tag.

IV. Methods of the Invention

A. Second Harmonic Generation

Second harmonic generation (SHG) is a nonlinear optical process, in which photons interacting with a nonlinear material are effectively "combined" to form new photons with twice the energy, and therefore twice the frequency and half the wavelength of the initial photons. It is a special case of sum frequency generation (SFG). Surface-selective nonlinear optical (SSNLO) techniques such as SHG allow the detection of interfacial molecules or particles in the presence of the bulk species. An intense laser beam (the fundamental) is directed on to the interface of some sample; if the interface is non-centrosymmetric, the sample is capable of generating nonlinear light, i.e. the harmonics of the fundamental. The fundamental or the second harmonic beams can easily be separated from each other, unlike the typical case in fluorescence techniques with excitation and emission light, which are separated more narrowly by the Stokes shift. Individual molecules or particles can be detected if they 1) are nonlinearly active (possess a hyperpolarizability) and 2) are near to the surface and through its influence (via chemical or electric forces) become non-randomly oriented. This net orientation and the intrinsic SHG-activity of the species are responsible for an SHG-allowed effect at the interface.

SHG has emerged as a sensitive technique to detect and study the conformational changes of biomolecules using SH-active probes (Salafsky, J. S. *Journal of Chemical Physics* 2006, 125, 074701; Salafsky, J. S. *Physical Chemistry Chemical Physics* 2007, 9, 5704). Labeled proteins that are adsorbed or covalently immobilized on surfaces produce an SHG signal, which is due to the average, net orientation of the nonlinear polarizability of the SHG label relative to the surface plane. Specifically, the SH intensity is given as $I_{SH}=G(\chi_s^{(2)})^2 I^2$, where $I_{SH}$ is the second harmonic intensity, G is a constant that depends on the experimental geometry and wavelength, and I is the intensity of the fundamental beam. The nonlinear susceptibility, $\chi_s^{(2)}$, carries the details of the SH-active molecules on the surface via the equation:

$$\chi_s^{(2)} = N_s \langle \alpha^{(2)} \rangle,$$

where $N_s$ is the surface density of the molecules, the brackets denote an orientational average, and $\alpha^{(2)}$ is their nonlinear polarizability, a quantum-mechanical property that determines the probability of producing a second harmonic photon from two, incident photons of the fundamental beam. Measurements of $\chi_s^{(2)}$ provide information about the orientation of a molecule on the surface. For example, when $\alpha^{(2)}$ is dominated by a single element $\zeta\zeta\zeta^{(2)}$ along the molecular axis $\zeta$ and the azimuthal distribution of the molecules are random in the plane of the surface, the only elements of $\chi_s^{(2)}$ that do not vanish are:

$$\chi_{s\perp\perp\perp}^{(2)} = N_s \langle \cos^3\theta \rangle \alpha_{\zeta\zeta\zeta}^{(2)}$$

$$\chi_{s\perp\|\|}^{(2)} = \chi_{s\|\perp\|}^{(2)} = \chi_{s\|\|\perp}^{(2)} = \frac{1}{2} N_s \langle \cos\theta \sin^2\theta \rangle \alpha_{\zeta\zeta\zeta}^{(2)}$$

where $\theta$ is the polar angle between $\zeta$ and the surface normal, and the subindices $\perp$ and | refer to the directions perpendicular and parallel to the surface, respectively (Heinz, T. F., et al., *Physical Review A* 1983, 28, 1983).

The SH light is coherent and directional, so collection and isolation of the SH beam is simplified, and because the fundamental and the second harmonic are well separated spectrally, cross-talk, which can plague fluorescence measurements, is non-existent with SHG. Photodegradation of the probe occurs relatively slowly via two-photon-induced absorption, allowing measurements over relatively long timescales. The trade-off with SHG is signal strength—it is orders of magnitude weaker than fluorescence. However, only SH-active molecules immobilized on the surface contribute second harmonic light since randomly diffusing molecules near the surface produce no signal; their orientational average, from Equation 1, is zero. Therefore, SHG is intrinsically equipped to discriminate between surface-bound and free molecules. The SH signal reports on the orientational average of the probes, and thus changes due to conformational change.

The apparatus for detection of target protein—allosteric modulator interactions and their effects on target protein conformational structure can assume a variety of configurations. In its most simple form, the apparatus will comprise the following: i) a source of the fundamental light; ii) a substrate with surface-attached probes (such as an SHG-labeled target protein); and iii) a detector for measuring the intensity of the second harmonic or other nonlinear optical beams. More elaborate versions of the apparatus will employ, for example: a monochromator (for wavelength selection), a pass-filter, color filter, interference or other spectral filter (for wavelength selection or to separate the fundamental(s) from the higher harmonics), one or more polarizing optics, one or more mirrors or lenses for directing and focusing the beams, computer control, or software.

The mode of delivering or generating the nonlinear optical light (e.g., SHG) can be based on one or more of the following means: TIR (Total internal reflection), Fiber optics (with or without attached beads), Transmission (fundamental passes through the sample), Reflection (fundamental is reflected from the sample), scanning imaging (allows one to scan a sample), confocal imaging or scanning, resonance cavity for power build-up, multiple-pass set-up.

Measured information can take the form of a vector which can include one or more of the following parameters: intensity of light (typically converted to a photovoltage by a PMT or photodiode), wavelength of light (determined with a monochromator and/or filters), time, or position. Two general configurations of the apparatus are: image scanning (imaging of a substrate—intensity, wavelength, etc. as a function of x,y coordinate) and spectroscopic (measurement of the intensity, wavelength, etc. for some planar surface or for a suspension of cells, liposomes or other particles).

The fundamental beam can be delivered to the sample in a variety of ways (See, e.g., U.S. Patent Application Publication No.: 2002/0094528, the disclosure of which is incorporated by reference herein in its entirety). It is understood that in sum- or difference-frequency configurations, the fundamental beams will be comprised of two or more beams, and will generate, at the interfaces, the difference or sum frequency beams.

According to another aspect, charge-coupled detectors (CCD) array detectors can be used when information is desired as a function of substrate location (x,y). CCDs comprise an array of pixels (i.e., photodiodes), each pixel of which can independently measuring light impinging on it. For a given apparatus geometry, nonlinear light arising from a particular substrate location (x,y) can be determined by measuring the intensity of nonlinear light impinging on a CCD location (Q,R) some distance from the substrate—this can be determined because of the coherent, collimated (and generally co-propagating with the fundamental) nonlinear optical beam) compared with the spontaneous, stochastic and multi-directional nature of fluorescence emission. With a CCD array, one or more array elements (10) in the detector will map to specific regions of a substrate surface, allowing for easy determination of information as a function of substrate location (x,y). Photodiode detector and photomultiplier tubes (PMTs), avalanche photodiodes, phototransistors, vacuum photodiodes or other detectors known in the art for converting incident light to an electrical signal (i.e., current, voltage, etc.) can also be used to detect light intensities. For CCD detector, the CCD communicates with and is controlled by a data acquisition board installed in the apparatus computer. The data acquisition board can be of the type that is well known in the art such as a CIO-DAS16/Jr manufactured by Computer Boards Inc. The data acquisition board and CCD subsystem, for example, can operate in the following manner. The data acquisition board controls the CCD integration period by sending a clock signal to the CCD subsystem. In one embodiment, the CCD subsystem sets the CCD integration period at 4096 clock periods. By changing the clock rate, the actual time in which the CCD integrates data can be manipulated. During an integration period, each photodiode accumulates a charge proportional to the amount of light that reaches it. Upon termination of the integration period, the charge is transferred to the CCD's shift registers and a new integration period commences. The shift registers store the charges as voltages which represent the light pattern incident on the CCD array. The voltages are then transmitted at the clock rate to the data acquisition board, where they are digitized and stored in the computer's memory. In this manner, a strip of the sample is imaged during each integration period. Thereafter, a subsequent row is integrated until the sample is completely scanned.

In one aspect, the detector of the SH light can be a photomultiplier tube operated in single-photon counting mode. Photocurrent pulses can be voltage converted, amplified, subjected to discrimination using a Model SR445 Fast Preamplifier and Model SR 400 Discriminator (supplied by Stanford Research Systems, Inc.) and then sent to a counter. Photon counter gating and galvo control through a DAC output can be synchronized using a digital delay/pulse generator. Communication with a PC computer can be accomplished according to multiple methods as known to one skilled in the art, including but not limited to using a parallel register, a CAMAC controller card, and a PC adapter card.

In an alternative aspect, a bandpass, notch, or color filter is placed in either or all of the beam paths (e.g. fundamental, second harmonic, etc.) allowing, for example, for a wider spectral bandwidth or more light throughput. In one embodiment, an interference, notch-pass, bandpass, reflecting, or absorbent filter can be used in place of the filters in the figures in order to either pass or block the fundamental or nonlinear optical beams.

In some aspects of the methods provided herein, data recorded by the detector may be recorded on a fixed or data storage medium that is accessible via a system for reading the storage medium. For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of an active site of this invention using a program such as QUANTA. Output hardware might also include a printer, so that hard copy output may be produced, or a disk drive, to store system output for later use.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

A person having skill in the art will appreciate that any other method or technique to communicate or store data is also contemplated for providing real time data of target protein conformational changes upon binding a candidate modulator in a machine readable format.

B. SHG Detection and Labeling

A beam from a Ti:S femtosecond laser is used as the fundamental according to procedures known to those skilled in the art. Specifically, an argon-pumped Ti:sapphire system operating at 80 MHz with ~150 fs pulse duration and 0.5 W average power was employed (Coherent, Inc.). The beam is preferentially focused to a spot at the slide-buffer interface. Second harmonic light generated by the surface is collected, filtered from the fundamental, and detected by a photomultiplier tube (PMT) according to procedures known to those skilled in the art. A baseline signal with declining intensity due to photobleaching is recorded. The polarization of the fundamental beam was varied to produce the maximum signal output. The signal was verified as the second harmonic by determining its quadratic dependence on the fundamental intensity and measuring its characteristic spectral lineshape. Each data point was obtained by using a photon counting 1-second integration time.

In some aspects, the target protein can be labeled with a second harmonic (SH) active label, such as any of the labels described above. In one embodiment, the target protein is labeled with a second harmonic-active moiety (such as, a label) on one or more of the protein's amino acid residues and attached to a surface or oriented at an interface, such as any of the surfaces or interfaces described herein, so that the SH active label possesses a net orientation with respect to the interface. The labeled amino acid can include, but are not limited to, cysteine residues, lysine residues, or amines. In other embodiments, the target protein is labeled with an unnatural amino acid, such as, but not limited to Aladan. In some embodiments, a native amino acid residue in the target protein is labeled with the second harmonic-active label. In other embodiments, the labeled amino acid residue can be a mutated or substituted amino acid residue (such as a conservatively mutated or a conservatively substituted amino acid residue) engineered into the primary amino acid sequence of the target protein. In other embodiments, the target protein is attached to a surface (such as any of the surfaces or interfaces described herein) and labeled with an SH active label in situ.

C. Methods for Identifying Agents that Bind to Allosteric Sites on Target Proteins Provided herein are methods for identifying an agent that binds to an allosteric site on a target protein. A target protein bound to an SH active label with a net orientation at an interface is pre-incubated with a natural or synthetic ligand that is known to bind to the target protein's active site and a baseline second harmonic signal is established. Alternatively, the target protein is isolated from a cell or tissue with a natural ligand already bound to the active site. Following this, the target protein is incubated with a candidate allosteric modulator (such as any of the candidate allosteric modulator agents described herein). Binding of a candidate allosteric modulator to the target protein produces a detectable signal indicating a conformational change in the structure of the target protein. The presence or absence of a detectable SHG signal, therefore, identifies the candidate agent as an allosteric modulator of the target. In some embodiments, the synthetic ligand that is known to bind to the target protein's active site is a drug, such as an inhibitor or a synthetic analogue of the target protein's natural ligand.

In some aspects, the SH active label is bound to particular amino acid residues on the target protein known to bind one or more intracellular or extracellular ligands. These can include, without limitation, another protein, a peptide, a nucleic acid (such as an inhibitory nucleic acid, for example, an antisense oligonucleotide or an siRNA), a phospholipid, a carbohydrate, or a co-factor (such as, but not limited to, a metal ion or a vitamin). In one embodiment, an SH active label is bound to amino acids in a target protein known to be located in an interfacial zone of interaction between the target protein and another protein (i.e., located at a site of protein-protein interaction).

In some aspects, the labeled amino acid residues on the target protein can include, but are not limited to, cysteine residues, lysine residues, or amines. In other embodiments, the target protein is labeled with an unnatural amino acid, such as, but not limited to Aladan or Dansylalanine. In another embodiment, the unnatural amino acid is sum-frequency generation-active (SFG-active). In some embodiments, a UAA comprising a unique probe with tailored vibrational properties can be engineered into a target protein at a discrete site (such as an interfacial zone of interaction between the target protein and another protein) to identify site-specific conformational changes by SFG. Probe moieties can include, but are not limited to, NO, CN, SCN or $N_3$. In some embodiments, the probe moieties provide unique vibrational signatures in the spectral range between about 1,900 and 2,300 $cm^{-1}$. In some embodiments, a native amino acid residue in the target protein is labeled with the second harmonic-active label. In other embodiments, the labeled amino acid residue can be a mutated or substituted amino acid residue (such as a conservatively mutated or a conservatively substituted amino acid residue) engineered into the primary amino acid sequence of the target protein.

In other aspects, the target protein can be bound to a surface or at an interface, such as any of the surfaces or interfaces described above. In some embodiments, the target protein includes an affinity tag (such as, but not limited to, a polyhistidine tag, for example $His_6$) for immobilizing it onto the surface. In another embodiment, the surface is coated with nickel-oligo-PEG molecules for immobilizing a $His_6$-tagged kinase to the surface for SHG or SFG detection. In yet another embodiment, the surface is a supported lipid bilayer surface or a lipid analog bilayer surface.

In some aspects, binding of a candidate allosteric modulator agent to a SH active labeled target protein can induce a conformational change in the structure of the target protein. In some embodiments, this conformational change can cause the net orientation of the SH active label to change relative to the interface. In some embodiments, the net orientation of the SH active label changes any of about 1°, 2°, 3°, 4°, 5°, 6°, 7°, 8°, 9°, 10°, or more relative to the interface upon binding to a candidate allosteric modulator agent. In one embodiment, this change is detected and recorded in real time.

C. Methods for Identifying a Specific Site in the Structure of a Target Protein that Undergoes a Conformational Change Upon Allosteric Binding to an Agent Provided herein are methods for identifying a specific site in the structure of a target protein that undergoes a conformational change upon allosteric binding to an agent. In some aspects, a single target protein is labeled with an SH active label at two or more different locations, such that each target protein is bound to one SH active label but the location of the SH active label between at least two or more target proteins differ (i.e, at least two copies of a target protein each has a single SH active label located in a different region of the target protein). The at least two target proteins bound to SH active labels with net orientations at an interface can optionally be pre-incubated with a natural or synthetic ligand that is known to bind to the target protein's active site and a baseline second harmonic signal is established. Each of the at least two or more labeled target proteins are then incubated with a candidate allosteric modulator agents (such as any of the candidate allosteric modulator agents described herein). Binding of a candidate allosteric modulator to the target protein produces a detectable signal indicating a conformational change in the structure of the target protein. If a target protein labeled with an SH active label located at a first site on the target produces a detectable signal upon binding to a candidate allosteric modulator, whereas no detectable signal is produced upon incubating the same candidate allosteric modulator with the target protein labeled with an SH active label located at a second site on the target, this indicates that the candidate allosteric modulator binds specifically to the target protein and induces a conformational change at the first site on the target protein and not at the second site. On the other hand, if the target protein with an SH active label located at a first site and the target protein with an SH active label located at a second site each produce a detectable signal upon incubation with a candidate allosteric modulator, this indicates either that the candidate allosteric modulator is specifically binding to the target protein and inducing a conformational change in the structure of the target protein at both sites or that the candidate allosteric modulator is binding non-specifically to the target protein. Increasing the number of sites on the target protein wherein SH active labels are positioned can increase the ability to determine whether a candidate allosteric modulator binds specifically or non-specifically to a target protein (i.e. the likelihood of a specific interaction decreases with the number of detectable signals produced over more than one, such as two, three, four or five, sites on a target protein). In some embodiments, several versions of the target protein can be produced, such as any of 1, 2, 3, 4, 5, 6, 7, 8, 9, or 10, or more, each having an SH active label located in a different region of the target protein.

The term "specific binding" describes the generally specific and reversible interactions between a target biomolecule (e.g., a target protein) and a binding partner requiring the combined effects of spatial complementarity of biomolecule and binding partner structures at a binding site coupled with one or more type of electrostatic forces, hydrogen bonding, hydrophobic forces, and/or van der Waals forces at the binding site. The greater the spatial complementarity and the stronger the other forces at the binding site, the greater will be the binding specificity of a biomolecule for its respective binding partner.

The term "non-specific binding" refers to the interactions between a target biomolecule and a binding partner through non-specific interactions, e.g., through electrostatic forces, hydrogen bonding, hydrophobic forces, and/or van der Waals forces at an interaction site, but lacking the structural complementarity that enhances the effects of the non-structural forces such as in affinity (specific) binding.

In some embodiments, a first change in a detectable signal (e.g., a normalized SHG intensity) upon binding of a candidate binding partner to a target biomolecule is measured when the target biomolecule is labeled at a first site (e.g., a first amino acid site). In some embodiments, a second change in a detectable signal (e.g., a normalized SHG intensity) upon binding of the same candidate binding partner to a target biomolecule is measured when the target protein is labeled at a second site (e.g., a second amino acid site). A normalized SHG intensity is the ratio of the SHG signal measured upon binding of a candidate binding partner to a target biomolecule to a control value (e.g., the SHG signal measured in the absence of the candidate binding partner).

In some embodiments, a difference between the first change and the second change above noise level indicates that the candidate binding partner is a specific binder. In some embodiments, the noise level is 0.1, 0.2, 0.5, 1, 2, 3, 4, 5, or 10%. In some embodiments, the difference between the first change and the second change is 1%, 2%, 3%, 5%, 10%, 20%, 30%, 40%, 50%, 60%, 70%, 80%, 90%, 100%, 200%, 300%, or 500% above noise level. In some embodiments, the specific binding partner has an affinity for the target biomolecule in the range of $10^{-4}$-$10^{-8}$M, $10^{-4}$-$10^{-8}$M, $10^{-4}$-$10^{-5}$M, $10^{-5}$-$10^{-6}$M, $10^{-6}$-$10^{-7}$M, $10^{-7}$- $10^{-8}$M, $10^{-8}$-$10^{-12}$M, $10^{-8}$-$10^{-9}$M, $10^{-9}$-$10^{-10}$M, $10^{-10}$-$10^{-11}$M, $10^{-11}$-$10^{-12}$M, or more than $10^{-4}$, $10^{-5}$, $10^{-6}$, $10^{-7}$, $10^{-8}$, $10^{-9}$, $10^{-10}$, $10^{-11}$, or $10^{-12}$ in free solution.

In some embodiments, a difference between the first change and the second change below noise level indicates that the candidate binding partner is a non-specific binder. In some embodiments, the noise level is 0.1, 0.2, 0.5, 1, 2, 3, 4, 5, or 10%. In some embodiments, the difference between the first change and the second change is 95%, 85%, 75%, 65%, 55%, 45%, 35%, 25%, 15%, 5%, 4%, 3%, 2%, 1%, 0.5%, 0.2%, or 0.1% below noise level. In some embodiments, the non-specific binding partner has an affinity for the target biomolecule in the range of $10^{-1}$-$10^{-2}$M, $10^{-2}$-$10^{-3}$M, $10^{-3}$-$10^{-4}$M, or less than $10^{-4}$, $10^{-3}$, $10^{-2}$, or $10^{-1}$ in free solution.

In some aspects, at least one of the SH active labels is not bound to a native amino acid residue on the target protein but is, rather, bound to an amino acid engineered into a specific region of the target protein (e.g., an engineered cysteine residue). In some embodiments, the target protein is labeled by an SH active label on more than one native amino acid residues (such as a cysteine residue), wherein each native amino acid is located in a different region or domain of the target protein.

In another embodiment, all of the SH active labels on the target protein are bound to engineered (i.e. mutated or substituted) amino acid residues in two or more regions of the target protein.

In some aspects, the labeled amino acid residues on the target protein can include, but are not limited to, cysteine residues, lysine residues, or amines. In other embodiments, the target protein is labeled with an unnatural amino acid, such as, but not limited to Aladan or Dansylalanine. In another embodiment, the unnatural amino acid is sum-frequency generation-active (SFG-active). In some embodiments, a UAA comprising a unique probe with tailored vibrational properties can be engineered into a target protein at a discrete site (such as an interfacial zone of interaction between the target protein and another protein) to identify site-specific conformational changes by SFG. Probe moieties can include, but are not limited to, NO, CN, SCN or $N_3$. In some embodiments, the probe moieties provide unique vibrational signatures in the spectral range between about 1,900 and 2,300 $cm^{-1}$. In some embodiments, a native amino acid residue in the target protein is labeled with the second harmonic-active label. In other embodiments, the labeled amino acid residue can be a mutated or substituted amino acid residue (such as a conservatively mutated or a conservatively substituted amino acid residue) engineered into the primary amino acid sequence of the target protein.

In other aspects, the target protein can be bound to a surface or at an interface, such as any of the surfaces or interfaces described above. In some embodiments, the target protein includes an affinity tag (such as, but not limited to, a polyhistidine tag, for example $His_6$) for immobilizing it onto the surface. In another embodiment, the surface is coated with nickel-oligo-PEG molecules for immobilizing a $His_6$-tagged proteins (such as a kinase) to the surface for SHG or SFG detection. In yet another embodiment, the surface is a supported lipid bilayer surface or a lipid analog bilayer surface.

In some aspects, binding of a candidate allosteric modulator agent to a SH active labeled target protein can induce a conformational change in the structure of the target protein. In some embodiments, this conformational change can cause the net orientation of the SH active label to change relative to the interface. In some embodiments, the net orientation of the SH active label changes any of about 1°, 2°, 3°, 4°, 5°, 6°, 7°, 8°, 9°, 10°, or more relative to the interface upon binding to a candidate allosteric modulator agent. In one embodiment, this change is detected and recorded in real time.

Provided herein are methods for determining specificity of a binding interaction between a target biomolecule and a candidate binding partner. In some examples, the target biomolecule is labeled at a first site with a non-linear active label such as a second harmonic-active moiety. The labeled protein is then contacted with a candidate binding partner. Using a surface selective technique, a signal (e.g., a normalized second harmonic generation intensity) associated with the binding between the target biomolecule and the candidate binding partner is measured.

The same procedure is then repeated for one or more sites. For example, the target biomolecule can be labeled at a second site (without labeling the first site) before it is contacted with the same candidate binding partner. Using a surface selective technique, a signal (e.g., a normalized second harmonic generation intensity) associated with the binding between the target biomolecule and the same candidate binding partner is measured. The signal generated using the target labeled at the first site is compared to the signal generated using the target labeled at the second site. A difference above noise level (e.g., 1%, 2%, 3%, 5%, 10%, 20%, 30%, 40%, 50%, 60%, 70%, 80%, 90%, 100%, 200%, 300%, or 500% above noise level) indicates specific binding between the target biomolecule and the candidate binding partner. A difference below noise level indicates non-specific binding between the target biomolecule and the candidate binding partner.

The methods provided herein can be used to screen a library of drug candidates targeting a same target biomolecule. For example, the procedure outlined above can be carried out for each drug in the library. For each drug, a signal (e.g., a normalized second harmonic generation intensity) associated with the binding between the target biomolecule and the drug candidate is measured once when the target biomolecule is labeled on the first labeling site, and once when the target biomolecule is labeled on the second labeling site (without labeling the first site). The difference between these two measurements is an indication of the binding specificity of the drug candidate, its ability to induce conformation in the target biomolecule, pharmacokinetics and efficacy. Based on the differences between these two measurements, a drug candidate can be selected for additional downstream screening (e.g., animal test or clinical trial).

The target biomolecule can be any biomolecule including a protein, a DNA, a RNA, or an oligosaccharides.

The labeling sites can be selected based on several criteria. For example, they can be selected based on the distances from the binding site. In some methods, the first labeling site is more proximal to the binding site than the second labeling site is. The first labeling site and the second labeling site can be both within the binding interface. Preferably, not all of the labeling sites are within the binding interface. In some methods, at least one of the labeling site is not within the binding interface. In other methods, at least one of the labeling site is within the binding interface. In some methods, the first labeling site is within the binding interface and the second site is outside the binding interface. In some methods, both labeling sites are outside the binding interface.

D. Methods for Identifying an Agent that Binds to an Allosteric Site on a G Protein-Coupled Receptor (GPCR)

Provided herein are methods for identifying an agent that binds to an allosteric site on a G protein-coupled receptor (GPCR; such as any of the GPCRs described herein). A GPCR is pre-incubated with a natural ligand, wherein the natural ligand is labeled with a second harmonic-active label that has a net orientation at an interface upon binding to the GPCR and a baseline second harmonic signal is established. Following this, the GPCR is incubated with a candidate allosteric modulator (such as any of the candidate allosteric modulator agents described herein). Binding of a candidate allosteric modulator to the GPCR produces a detectable signal indicating a conformational change in the structure of the GPCR. The presence or absence of a detectable SHG signal, therefore, identifies the candidate agent as an allosteric modulator of the GPCR. In some embodiments, the natural ligand that is known to bind to the GPCR's active site is a hormone, such as a peptide hormone.

In some aspects, the labeled amino acid residues on the natural ligand can include, but are not limited to, cysteine residues, lysine residues, or amines. In other embodiments, the natural ligand is labeled with an unnatural amino acid, such as, but not limited to Aladan or Dansylalanine. In another embodiment, the unnatural amino acid is sum-frequency generation-active (SFG-active). In some embodiments, a UAA comprising a unique probe with tailored vibrational properties can be engineered into a natural ligand at a discrete site. Probe moieties can include, but are not limited to, NO, CN, SCN or $N_3$. In some embodiments, the probe moieties provide unique vibrational signatures in the spectral range between about 1,900 and 2,300 $cm^{-1}$. In some embodiments, a native amino acid residue in the natural ligand is labeled with the second harmonic-active label. In other embodiments, the labeled amino acid residue can be a mutated or substituted amino acid residue (such as a conservatively mutated or a conservatively substituted amino acid residue) engineered into the primary amino acid sequence of the natural ligand.

In other aspects, the GPCR can be expressed on the plasma membrane of a biological cell or a synthetic biological membrane, such as on the surface of a liposome. In yet another embodiment, the GPCR is embedded within a surface such as a supported lipid bilayer surface or a lipid analog bilayer surface. In some embodiments, the biological cell naturally expresses the GPCR on its surface. In other embodiments, the biological cell heterologously expresses a nucleic acid encoding a GPCR which is expressed on the surface of the biological cell. Methods for the heterologous expression of proteins (such as GPCRs) on the surface of cells are numerous and well known techniques in the art.

In some aspects, binding of a candidate allosteric modulator agent to a GPCR can induce a conformational change in the structure of the GPCR. In some embodiments, this conformational change can cause the net orientation of the SH active labeled-natural ligand to change relative to the interface (e.g., the plasma membrane of a cell or a synthetic biological membrane, such as a liposome. In some embodiments, the net orientation of the SH active label changes any of about 1°, 2°, 3°, 4°, 5°, 6°, 7°, 8°, 9°, 10°, or more relative to the interface upon binding to a candidate allosteric modulator agent. In one embodiment, this change is detected and recorded in real time.

V. Labeling

Labels can be attached to different types of labeling sites on proteins. For example, one or more labels can be attached to native protein residues or mutant protein sites (e.g., a site incorporating an unnatural amino acid), or a combination thereof. The labeling sites can be located on the surface of the protein or buried within the protein. Preferably, the labeling sites are located on the protein surface. Labels attached to unnatural amino acids allow labeling a residue buried within the protein.

Labels can be attached to any type of amino acid residues. For example, the labels can be attached to a pre-selected site such as cysteine residue or a lysine residue. The labels can also be randomly attached to the amino acids throughout the protein (e.g., via an amino group). Labels can bind to different residues (e.g., cysteine or lysine residues) at different rates or different occupancy. For example, labels in solution can bind to an amine group at one site faster than an amine group at another site. The binding rates also depend on the labeling reaction conditions. For example, a change in pH can mean that one type of residue will preferentially bind a given label. Further, the ratio of labels (e.g., dye molecules) to the proteins to be labeled can affect the number of sites that are labeled. Controlling the number and/or location of labeled sites can be important, for example, for probing the specificity of binding interactions. For unnatural amino acids, the labeling procedure can be specifically tailored for labeling selected sites. Such sites can be selected strategically, such as, for example, in the vicinity of functionally relevant sites.

In some examples, one or more labeling sites can be made more available for labeling for example by immobilizing the protein to be labeled on a lipid bilayer, thus exposing a portion of the protein that faces away from the lipid bilayer. Thus, labeling can be performed randomly and/or specifically with respect to preselected locations on the protein. For example, 1, 2, 3, 4, 5, 6, 7, 8, 9, 10, 20, 30, 40, 50, 75, 100 or more labels can be provided near or surrounding a preselected location (such as a functionally relevant site).

The labeled proteins can be assayed using various formats. For example, the labeled proteins can be assayed using a multi-well plate. Proteins in the wells can be labeled in different ways (i.e., at different labeling sites). Assaying differently labeled proteins can provide a map of the protein conformational changes upon binding to a binding partner. In some methods, the labeling sites can be selected so that the sites form a predetermined pattern or grid on or within the protein. The conformational changes detected at different labeling sites can indicate specificity of the binding of the binding partner.

V. Kits

In other aspects, kits comprising compositions for use in the practice of the methods disclosed herein form another feature of the invention. Any description of methods, kits and/or systems (e.g., including any of the labels and/or unnatural amino acids described herein) herein using second harmonic generation (SHG) may be applied to methods, kits and/or systems using sum frequency generation (SFG) or difference frequency generation (DFG).

In one embodiment, kits comprising one or more SHG, SFG or DFG-active moieties (such as labels) for conjugation to target proteins, such as any of the SHG, SFG or DFG-active labels (such as dye labels) described herein, are provided. These can include dye labels with different coupling chemistries for specific functional groups such as, but not limited to, maleimide labels (such as, PyMPO-MALEIMIDE™ (1-(2-Maleimidylethyl)-4-(5-(4-Methoxyphenyl)Oxazol-2-yl) Pyridinium Methanesulfonate)), PyMPO-NHS, oxazole labels, BADAN™ (6-Bromoacetyl-2-Dimethylaminonaphthalene), PyMPO-SE™ (1-(3-(Succinimidyloxycarbonyl)Benzyl)-4-(5-(4-Methoxyphenyl)Oxazol-2-yl)Pyridinium Bromide), and ACRYLODAN™ (6-Acryloyl-2-Dimethylaminonaphthalene). In other embodiments, the dyes can be coumarin-based dyes such as, but not limited to, ketocoumarin, and 3,3'-carbonyl bis (7-diethylaminocoumarin).

Also contemplated for inclusion in a kit are tools and reagents for labeling proteins with SHG, SFG or DFG-active labels for use in any of the methods disclosed herein. These can include, without limitation, buffer panels for testing different labeling conditions, buffers for performing a labeling reaction, tubes in which to carry out labeling reactions, spin columns and/or gel filtration columns for purifying labeled protein from unbound label, and buffers for washing the labeled protein.

In another embodiment, the kits can comprise one or more surfaces for binding a target protein, such as any of the surfaces disclosed herein. These surfaces can either be reusable or consumable (i.e. intended for one or a limited number of uses). The surfaces can be made of glass (such as a glass slide), plastic, metal, latex, rubber, ceramic, polymer (such as, but not limited to, polypropylene, polyvinylidene difluoride, polystyrene, or polyethylene (for example, polyethylene glycol)) or any surface to which biological molecules (such as proteins) can adsorb or be attached. In some embodiments, the surfaces are smooth. However, in other embodiments, the surfaces can include preformed surface features, such as, but not limited to, trenches, v-grooves, mesa structures, and/or wells. Additionally, the surfaces can be pre-cleaned according to any of the methods disclosed herein. In additional embodiments, where the surface does not include preformed surface features, the kits can contain adhesive gaskets for templating wells on the surface.

In one embodiment, the surfaces included in the kit can be optimized for different excitation geometries, wherein the mode of delivering or generating nonlinear optical light is based on, without limitation, one or more of TIR (total internal reflection), transmission, or reflection.

In a further embodiment, the surfaces included in the kits disclosed herein can be pre-coated with one or more molecules which provide a surface chemistry suitable for attachment to a target protein. These molecules can include any of those disclosed herein such as, but not limited to, aldehyde silanes, BSA-NHS (BSA-N-hydroxysuccinimide), or oligopolyethylene glycol (PEG). In one embodiment, the molecule can include an affinity tag, such as any of those disclosed herein. For example, the surface can be coated with nickel-oligo-PEG molecules for immobilizing histidine-tagged proteins to the surface.

In another embodiment; the surfaces included in the kits can be pre-coated with a supported lipid (such as, but not limited to, phospholipid) bilayer or supported lipid analog bilayer. This embodiment of the kits also includes lipids or mixtures of lipids for use in preparing supported lipid bilayers or supported lipid analog bilayers on any of the surfaces disclosed herein. In some embodiments, the lipid mixture can comprise phosphocholine such as, but not limited to, DOPC. In some embodiments, the lipid mixture can comprise, without limitation, one or more of DDAB (N,N-distearyl-N,N-dimethylammonium bromide), DMRIE (N-(1,2-dimyristyloxyprop-3-yl)-N,N-dimethyl-N-hydroxyethyl ammonium bromide), DODAC (N,N-dioleyl-N,N-dimethylammonium chloride), DOGS (diheptadecylamidoglycyl spermidine) DOPE (1,2-sn-dioleoylphoshatidyethanolamine), DOSPA (N-(1-(2,3-dioleyloxyl)propyl)-N-(2-(sperminecarboxamido)ethyl)-N,N-dimethylammonium trifluoroacetate), DOTAP (N-(1-(2,3-dioleyloxyl)propyl)-N,N,N-trimethylammonium chloride), DOTMA N-(1-(2,3-dioleyloxyl)propyl)-N,N,N-trimethylammonium chloride). In a further embodiment, any of the lipids or lipid components of lipid mixtures can include an affinity tag for binding to proteins (such as, but not limited to, a nicklated lipid, for example, DOGS-Ni-NTA lipids).

Also contemplated for inclusion in one or more of the kits disclosed herein are signal peripherals for use with an apparatus for detection of target protein-allosteric modulator interactions and effects on target protein conformational structure, for determining specificity of a binding interaction between a target biomolecule and a candidate binding partner, and/or any detection and/or measurement methods of conformational change using SHG, SFG or DFG. These can include, without limitation, a pass-filter, a color filter, an interference or other spectral filter (for wavelength selection or to separate the fundamental(s) from higher harmonics), one or more polarizing optics, and/or one or more mirrors or lenses for directing and focusing beams. Motorized rotational stages for purposes of making quantitative measurements can also be included in the kits disclosed herein.

In another embodiment, one or more co-factors necessary for protein or enzymatic function can be included in the kits disclosed herein. These can include inorganic co-factors (such as, but not limited to, copper, iron, magnesium, manganese, molybdenum, nickel, cobalt, or zinc ions). These can also include organic cofactors such as, but not limited to, thiamine pyrophosphate, $NAD^+$ (NADH), $NADP^+$ (NADPH), pyridoxal phosphate, lipoamide, methylcobalamin, cobalamine, biotin, Coenzyme A, tetrahydrofolic acid, menaquinone, ascorbic acid, flavin mononucleotide, flavin adenine dinucleotide, Coenzyme F420, adenosine triphosphate (ATP), adenosine diphosphate (ADP), guanosine triphosphate (GTP), guanosine diphosphate (GDP), S-adenosyl methionine, Coenzyme B, Coenzyme M, Coenzyme Q, cytidine triphosphate, glutathione, heme, nucleotide sugars, pyrroloquinoline, quinone, and/or tetrahydrobiopterin. Also contemplated for inclusion in any of the kits disclosed herein are one or more labeled (such as SFG or SHG-labeled) peptides and/or proteins known to bind to one or more target proteins (for example, ubiquitin or SUMO) or one or more SFG or SHG-labeled antibodies or fragments thereof.

In still other embodiments, the kits can include one or more components for introducing SHG-, SFG-, or DFG-active unnatural amino acid (UAA) labels into proteins. These components can include, without limitation, cell free translation extracts, tRNA/tRNA-synthetase pairs for introducing a particular unnatural amino acid label (such as, Aladan) and/or reaction and wash buffers. In some examples, these components may allow labeling to be performed selectively in one or more locations on the target protein, such as, for example, for placement of labels in accordance with the specificity methods described herein, for placement of labels in strategic locations surrounding functionally relevant sites (e.g., sites located near a region of protein-protein interaction, sites not directly located near any binding site but affected conformationally by a binding event etc.), active sites, binding sites, or any other sites on or within the protein structure. The kits may include tools for achieving selective labeling at predetermined positions.

In another embodiment, the kits can include one or more components for live cell labeling. These can include, without limitation, surfaces for cell attachment, SHG and SFG-active labels, buffer for use in the cell labeling reaction, wash-out buffer for removing unreacted label, as well as cell growth media.

In yet another embodiment, the kits can include one or more components for labeling of native residues in accordance with labeling techniques described herein. Such components may include any of the components described for labeling of live cells, reaction and wash buffers, components for dosage of labels (e.g., dye) with respect to the protein to be labeled, and other components. For example, the components may allow for labeling conditions (e.g., label concentration, physical and/or chemical environment) to be varied in order to achieve a desired labeling result.

In some embodiments, one or more of the kits may contain components for labeling arrays, and/or for labeling multiple sample wells. For example, the components for dosage of labeling may enable different labeling results to be achieved in different wells and/or array regions based on precise control of labeling conditions. For example, the kits may include components for varying labeling conditions with position.

Further, the kits may include one or more labels that are provided together with corresponding labeling tools (e.g., one or more components for introducing SHG, SFG or DFG-active unnatural amino acid (UAA) labels into proteins). Such reagents may be included in custom concentrations or amounts in accordance with application area of the kit.

VI. Systems

In other aspects, provided herein are systems for using second harmonic generation (SHG), sum frequency generation (SFG), and/or difference frequency (DFG) techniques to screen for and identify agents which bind to and/or modulate allosteric sites on target proteins, to determine specificity of a binding interaction between a target biomolecule and a candidate binding partner, and/or to detect and/or measure conformational change.

In some embodiments, the system comprises a target protein labeled with an SHG-, SFG- or DFG-active moiety (such as any of the SFG-, SHG- or DFG-active moieties disclosed in any of the compositions, methods, or kits provided herein, for example, an SFG-, SHG- or DFG-active dye label or an SFG-, SHG- or DFG-active unnatural amino acid). The system also comprises an apparatus for detection of target protein-agent interactions comprising i) a source of the fundamental light; ii) a substrate with surface-attached probes (such as an SHG-labeled, SFG-labeled or DFG-labeled target protein); and iii) a detector for measuring the intensity of the second harmonic or other nonlinear optical beams. In some embodiments of the system, binding of an agent to an allosteric site on a protein is detected by the apparatus and data recorded by the detector can be recorded on a fixed or data storage medium that is accessible via a system for reading the storage medium. In other embodiments, specificity of a binding interaction between a target biomolecule and a candidate binding partner is detected by the apparatus and data recorded by the detector can be recorded on a fixed or data storage medium that is accessible via a system for reading the storage medium. In yet other embodiments, one or more real-time conformational change upon any binding event is detected and monitored (e.g., in real-time) and data recorded by the detector can be recorded on a fixed or data storage medium that is accessible via a system for reading the storage medium.

In other embodiments, the system further comprises a monochromator (for wavelength selection), a pass-filter, color filter, interference or other spectral filter (for wavelength selection or to separate the fundamental(s) from the higher harmonics), one or more polarizing optics, one or more mirrors or lenses for directing and focusing the beams, computer control, or software. In other embodiments, the mode of delivering or generating the nonlinear optical light (e.g., SHG) can be based on one or more of the following means: TIR (Total internal reflection), Fiber optics (with or without attached beads), Transmission (fundamental passes through the sample), Reflection (fundamental is reflected from the sample), scanning imaging, confocal imaging or scanning, resonance cavity for power build-up, or multiple-pass set-up.

In another embodiment of the system, measured information can take the form of a vector which can include one or more of the following parameters: intensity of light (typically converted to a photovoltage by a PMT or photodiode), wavelength of light (determined with a monochromator and/or filters), time, or position. Two general configurations of the apparatus are: image scanning (imaging of a substrate—intensity, wavelength, etc. as a function of x,y coordinate) and spectroscopic (measurement of the intensity, wavelength, etc. for some planar surface or for a suspension of cells, liposomes or other particles).

The invention can be further understood by reference to the following examples, which are provided by way of illustration and are not meant to be limiting.

EXAMPLES

Example 1

Identification of Allosteric Modulators of a Kinase by Addition of a Synthetic Ligand to the Kinase Active Site Kinases are a major class of drug targets with at least 30 distinct kinase targets currently in clinical trials. Most kinase drugs, known as type I inhibitors, bind to the kinase ATP binding site and work by mimicking and directly competing with ATP to stabilize the kinase activation loop into an active confirmation. Type II inhibitors, on the other hand, cause the activation loop of the kinase to shift into an inactive conformation by partially binding to the activation loop as well as other sites on the kinase. Type III kinase inhibitors, on the other hand, allosterically modulate kinase activity by binding to sites on the kinase other than the kinase activation loop. The identification of type III inhibitors is difficult, due to the fact that determination of the site of candidate inhibitor binding to a kinase typically requires X-ray crystallography to discern. In this example, second harmonic generation (SHG) detection is used to identify molecules that i) change kinase conformation at one or more labeled sites and ii) do so in the presence of a known synthetic ligand (imatinib) bound to the kinase active site, thereby biasing the search for allosteric molecules which by definition bind to a location outside the active site.

Materials and Methods

Kinase Production and Labeling

Abl kinase KD with a N-terminal 6×His tag is constructed, expressed and purified as described in the literature (5-7). The protein is then dialyzed in labeling buffer (0.1 M Tris buffer pH 8.0, 20 mM NaCl, 5 mM TCEP, 5% glycerol) by standard procedures. The protein concentration should be 2-5 mg/mL for labeling. Lower concentrations are acceptable but labeling time may need to be adjusted accordingly. Concentrating the protein by use of a Centricon may be necessary to raise the protein to this level of concentration.

The concentrated protein (2-5 mg/mL) is mixed with PyMPO-MALEIMIDE™ (1-(2-Maleimidylethyl)-4-(5-(4-Methoxyphenyl)Oxazol-2-yl)Pyridinium Methanesulfonate) (Invitrogen) at a molar ratio of 1:12. Maleimide probes are highly specific for cysteines. The DMSO concentration in the labeling reaction is limited to about 3% or less. The labeling reaction is then transferred to a clean conical glass labeling vial with a stir vane and the reaction placed inside foil wrap on a stir plate for 1 hour at room temperature with gentle stirring. The labeled protein is column purified using Zeba spin columns using manufacturer's published protocols in an aliquot of stacking buffer of Measurement/Loading buffer (0.1 M Tris, buffer pH 8.0 20 mM NaCl). The protein:dye stoichiometry is determined spectrophotometrically to be about 1:2 in this case. Mass spectrometry confirmed that the probe labeled two cysteines in the kinase.

Glassware and Sonicator Preparation

Clean all glassware with Piranha wash (20 minutes) prior to starting. Use caution. Piranha wash is highly exothermic and prone to explosion, especially when in contact with organics. Prepare a solution in heat-safe glassware such as Pyrex in fume hood by measuring out $H_2O_2$ first then adding acetic acid. Rinse vacuum bottles with Chloroform ($CHCl_3$). Determine desired molar ratio of DOPC lipid to DGS NTA (Ni) while taking care to avoid exposure to air as much as possible. Place vacuum bottle with lipid mix onto Rotovap evaporator. Evaporate until dry (about 30 seconds) and then blow $N_2$ gas over the evaporated preparation for 10 min to remove residual $CHCl_3$. Resuspended lipid mixture in 2 mL of di$H_2O$. Vortex vigorously until a cloudy suspension forms (about 5 minutes). Transfer the suspension to 4 mL polystyrene test tube. Sonicate the lipid mixture on ice until the solution clears. This should require about 60 to 90 seconds with the sonicator set to 25% power.

Transfer the sonicated lipid solution into microcentrifuge tubes and centrifuge at 17,000×G for 30 minutes at 4° C.

Transfer the supernatant into clean microcentrifuge tubes and store the finished lipid preps at 4° C. which are stable for about 1 month.

Slide Preparation and Protein Loading

Immediately before applying DOPC/DGS NTA (Ni) lipids, clean microscope slides with Piranha wash for 20 minutes. Rinse 3× with diH$_2$O in a slide staining vessel. Dry slides with compressed Nitrogen. Assemble SHG wells by attaching adhesive gaskets to Piranha-cleaned slides (i.e., 16 wells per slide containing 10-20 µl volume). Use an assembly jig to align gaskets, carefully lay slide into jig and press firmly. Dilute DOPC/DGS NTA (Ni) lipid prep 1:1 with PBS or TBS buffers. 100 mM NaCl is required to reduce hydrostatic charge of the glass slide and enable the SLB to form. Pipet 10 µL of diluted DOPC/DGS NTA (Ni) lipid into the wells of the slide and incubate for 5 minutes at room temperature. Wash the wells by submersing the slide in buffer bath (PBS or TBS) and agitating with a 200 µL pipettor taking care not to introduce air into the wells at any time. Exchange the entire volume of buffer in the bath with fresh buffer and repeat the washing step 2 more times. Add a 1:1 volume of 100 mM NiCl$_2$ solution to all wells and incubate for 10 minutes at room temperature. Wash the wells by submersing the slide in buffer bath (PBS or TBS) and agitating with a 200 µL pipettor. Exchange the entire volume of buffer in bath with fresh buffer and repeat the washing step 2 more times. If necessary, exchange the buffer in the wells to an appropriate protein loading buffer and load the target protein of interest onto the wells. Incubate for 30 to 90 minutes at room temperature followed by a thorough rinse of the wells with assay buffer before starting experiments.

SUVs are applied over Piranha-washed Fisher slides to make the SLB surface. NiCl2 was added for 10 minutes and wells were washed in labeling buffer.

Labeled protein is loaded onto the SLB surface prepared as describe above at 3 µM for 45 minutes, followed by washing. FIG. 1 shows that labeled protein can be detected by SHG on the SLB. If imidazole is added, the signal drops to the baseline level indicating that attachment to the surface occurs via the protein's His-tag.

Imatinib, which is known to bind to the active site pocket of Abl kinase by crystallography (6, 8, 9), is added to the well at a concentration of 5 µM and incubated for 10 minutes to allow binding to the ATP pocket (active site). A candidate allosteric modulator agent is then added to the well and the SHG signal is monitored for the candidate's ability to change conformation at the label sites. Positive 'hits' are identified as candidate allosteric modulators which change the baseline signal following their addition.

Example 2

Labeling a Site Located in a Region of a Target Protein which Participates in a Partner Binding Event Various mutations are made to insert cysteines in the region of H-Ras known to participate in PI3K effector binding. The native cysteine residue C118 can be optionally mutated to alanine or serine. The mutants are tested for an ability to be labeled by the SHG probe PyMPO-MALEIMIDE™ (1-(2-Maleimidylethyl)-4-(5-(4-Methoxyphenyl)Oxazol-2-yl)Pyridinium Methanesulfonate) using mass spectrometry and protocols known to those skilled in the art. For example, the native residue tyrosine Y64 is known to participate in PI3K binding. Accordingly, recombinant 6×-His-tagged (N-terminal) H-Ras protein with a double mutation (C118A, Y64C) are prepared according to standard protocols (10). H-Ras is labeled using the cysteine-reactive SHG probe, PyMPO-MALEIMIDE™ (1-(2-Maleimidylethyl)-4-(5-(4-Methoxyphenyl)Oxazol-2-yl)Pyridinium Methanesulfonate) in 0.1 M Tris pH 8.0, 20 mM NaCl, 0.5 mM TCEP, 5% glycerol and using a 12:1 dye:protein ratio for one hour at room temperature. Unreacted dye is purified away by gel filtration. Labeling of the cysteine at position 64 is confirmed by mass spectrometry. The protein is exposed to candidate binder molecules to identify only those candidate binder molecules that change Ras conformation at the site C64 in a significant way compared to the control (e.g., DMSO-buffer vehicle) as known to those skilled in the art. If the engineered cysteine cannot be labeled, sites that are functionally relevant in the effector binding event, as defined herein, are mutated and tested for an ability to be labeled. A similar procedure can be carried out for other the sites.

Example 3

Labeling a Target in Two or More Different Ways, where at Least One of the Two or More Different Ways does not Involve Labeling a Native Residue A slide with an oligo-PEG derivatization is prepared as follows: a slide-staining vessel is cleaned and dried in a vacuum oven at 75° C./20 inches Hg, and then allowed to cool to room temp. Enough SAT(PEG4) (N-Succinimidyl S-acetyl (thiotetraethylene glycol; Pierce) solution is added to the staining vessel to cover the entire slide (~50 mL). Ultrastick slides (amino-terminated silane derivatized slides; Thermo) are placed in a staining rack and submerged in the staining vessel. The slides are incubated in a hood at room temperature, stirring for 2-3 hrs. The slides are then removed from the SAT(PEG4) solution and transferred to a slide washing dish containing anhydrous chloroform. Sonicate the slides for 15 minutes by immersing washing dish to ⅔ its height in tap water. Transfer the slides to a second washing dish and rinse each with ethanol, then with diH$_2$0. Finally, set the cleaned SAT(PEG4) slides in vacuum oven at 37° C./20 inches Hg until dry (30 to 60 min).

Add 15 µL per well of deacylation solution containing 1 mg/ml maleimido-C3-NTA. Incubate 20 minutes at room temp under a glass cover. Wash thoroughly with diH$_2$0 followed by addition of 15 µL per well of 100 mM NiCl$_2$/Tris pH7.2 solution. Incubate 10 minutes at room temp. Wash wells by submersion in the Loading Buffer required by the specific experiment. Agitate with 200 µL pipettor. (However, if PBS is required by the experiment, wash NiCl$_2$/Tris pH7.2 solution out of wells with H$_2$O first, then wash with required buffer). Keep wells hydrated at all times with appropriate buffer.

A mutant of the protein dihydrofolate reductase (DHFR) with an N-terminal 8×His tag is created using methods known in the art (11-13). In the first case, a mutant is made in which both native cysteines are removed (C85A and C152A) and a single, different residue is mutated to cysteine. To select the site for the mutation, various residues on the surface of the protein are mutated to cysteine and tested for an ability to be labeled by an SHG probe. In the second case, the wild-type protein is labeled and attachment of the probe to C152 is confirmed by mass spectrometry. Wild type or recombinant protein is purified into 25 mM Tris pH 7.2, 150 mM NaCl. Either protein is labeled using PyMPO-MALEIMIDE™ (1-(2-Maleimidylethyl)-4-(5-(4-Methoxyphenyl)Oxazol-2-yl) Pyridinium Methanesulfonate) according to the following protocol. The protein is incubated in 25 mM Tris pH 7.2, 150 mM NaCl, 1 mM TCEP and 10% glycerol at ~50 uM with a 20:1 dye:protein labeling ratio (Final DMSO concentration is 5%). The protein is stirred overnight at 4° C. and then gel-purified into 25 mM Tris-HCl pH 7.2, 150 mM NaCl, 1 mM TCEP. The protein is immobilized to the PEG surface via its His-tag. Both proteins are exposed to the candidate binder molecules to assay whether the molecules change the protein's conformation at the different (cysteine) label sites. Comparing the SHG responses of the two differently labeled mutants can be used to determine, for example, the site-specific responses of a given candidate binding molecule on the target protein. For example, in cases where SHG responses from different labeling sites are identical, the candidate binding molecules could be binding to the protein non-specifically.

Example 4

Testing a Known Allosteric Modulator for Binding to Abl Kinase Via SHG Technology In this example, second harmonic generation (SHG) detection is used to investigate whether GNF-2, which is known to allosterically bind to Abl kinase based on X-ray crystallography studies (Nagar B, et al., Cell 2003; 112(6):859-871), induces a conformational change in the structure of Abl kinase upon binding. GNF-2 binding to both wildtype and a K419C mutant of Abl kinase were investigated.
Materials and Methods
Slide Cleaning and Assembly Glass slides were washed for 20 minutes in a Piranha Wash Solution (70% Sulfuric Acid/30% Hydrogen Peroxide) at 100° C. These were removed from heat and allowed to cool for 10 minutes. The slides were then removed from Piranha wash solution and the excess solution was permitted to drip from slide.

The slides were placed in a new container and washed 3× in $dH_2O$ (ultrapurified 18 MOhm) to remove any remaining Piranha solution. The slides were removed from the $dH_2O$ and dried by blowing Nitrogen gas over the slide.

An adhesive silicon isolator containing 16 wells was placed on the assembly jig and the dried slide placed onto the isolator followed by pressing down with a Kimwipe to firmly adhere.
Lipid Bilayers and Protein Loading A solution of Small Unilaminar Vesicles (SUV) was prepared by diluting the SUV stock solution (DOPC Lipid/DGS-NTA/DHPE Texas Red) 1:1 in PBS. 10 µL of this 1:1 SUV/PBS solution was placed into each well of the slide and incubates for 5 minutes at room temperature under a watch glass. The slides were then washed 3× by submerging the entire slide into a container with 50 mL of PBS. Each well was washed using PBS and two exchanges with a 200 µL tip. The slides were then removes from PBS and each well washed 3× with 20 µL of $dH_2O$. This step was necessary to prevent the $NiCl_2$ solution used in the next step from precipitating out of solution.

10 µL of a 0.1M $NiCl_2$ stock solution was placed into each well, producing a final solution of 0.05M $NiCl_2$ in the well. This was incubated for 10 minutes at room temperature under a watch glass.

The slides were washed once by submerging the entire slide into a container of 50 mL of PBS. Each well was washed using PBS and two exchanges with a 200 µL tip. The slides were then washed 3× by submerging the entire slide into a container with 50 mL of protein-specific reaction buffer (100 mM Tris, pH 8.0, 100 mM NaCl, 10 mM $MgCl_2$, 1 mM TCEP). Each well was washed using the reaction buffer and two exchanges with a 200 µL tip.

Ether 6× His-tagged Abl-KD or KD-K419C (Seeliger, et al., Structure. 2007; 15:299-311) was added to a final concentration of 5 µM in each well containing 8 µL of reaction buffer. The proteins were then permitted to incubate in the well for 45 minutes at room temperature under a watch glass.
SHG Assay GNF2 (Sigma Aldrich) was prepared as a 10 mM stock in DMSO. For the experiment, a 20 µM stock solution was prepared in reaction buffer with the reaction buffer having a 0.2% final DMSO concentration.

After 45 minutes, a slide was placed in the Artemis platform using BK-7 matching fluid to mount to the dove prism. Care was taken to remove any air bubbles from under the slide. Using the Artemis platform, a pre-wash linescan was performed to assess the SHG levels in each well.

Each well was then washed 5× with 20 µL of assay solution (100 mM Tris, pH 8.0, 100 mM NaCl, 10 mM $MgCl_2$, 1 mM TCEP, 0.2% DMSO).

Using the Artemis platform, a post-wash linescan was then performed to access the SHG levels in each well. The stage was moved to the selected well using the custom written software. Acquisition was started and data recorded for 5-7 seconds to determine the pre-buffer injection baseline.

10 µL of assay solution was injected into the well and mixed. The change in SHG levels was recorded for ~30s. Following this, laser output was blocked for ~5s to mark the period before GNF2 injection. The laser block was then removed and the SHG signal allowed to return to baseline levels. Data was then recorded for ~5 seconds followed by injection of 10 µL of 20 20 µM GNF2 stock solution into the well. The final concentration of GNF2 in the well was 10 µM. Data was then recorded for 30s post injection, laser output blocked for ~60s and then data recorded for an additional 30-60s.
Results The change in SHG levels was determined for both the buffer injection and GNF2 injection. The change was determined by taking the SHG intensity at 15s post injection and dividing by the baseline SHG intensity prior to injection.

The data from these experiments indicate that treatment of either wildtype Abl-KD or the K419C mutant with the Abl-kinase specific inhibitor GNF2 does not result in a conformational change as measured by SHG. While these Abl-KD fragments contain the domain necessary for GNF2 binding, these fragments lack the SH3-SH2 domain found in full length Abl-Kinase that is required for conformational change in response to GNF-2 binding as demonstrated in the peer reviewed publications listed below. Thus the SHG data show that no conformational change occurs upon binding GNF-2, as expected from prior X-ray co-crystal structure data. Therefore, this example indicates that SHG detection is a powerful and relatively fast technique for assessing allosteric binding of molecules to target proteins.

Example 5

Labeling a Protein at on Both Native Amine and Sulfhydryl Groups and Coupling to a Supported Lipid Bilayer This example demonstrates that a protein can be labeled on both native amine and sulfhydryl groups and coupled to a supported lipid bilayer via a histidine affinity tag for detection using SHG technology.

Materials and Methods

Preparation of Glassware and Sonicator: All glassware was cleaned with Piranha wash (20 minutes) prior to starting. Vacuum bottles were rinsed with Chloroform ($CHCl_3$). Desired molar ratio of DOPC lipid to DGS NTA(Ni) was then determined. For the data disclosed herein, 3% DGS NTA (Ni), 96.5% DOPC doped with 0.5% Texas Red DHPE for imaging the supported bilayers was used. A vacuum bottle with lipid mix was placed onto a Rotovap evaporator and evaporated until dry (about 30 seconds). $N_2$ gas was blown over the evaporated preparation for 10 min to remove any residual $CHCl_3$. The lipid mixture was then resuspended in 2 mL of $diH_2O$ and vortexed vigorously until a cloudy suspension formed (about 5 minutes). The suspension was transferred to a 4 mL polystyrene test tube. The lipid mixture was sonicated on ice until solution clears. The sonicated lipid solution was then transferred into microcentrifuge tubes and centrifuged at 17,000×G for 30 minutes at 4° C. The supernatant was then transferred into clean microcentrifuge tubes. Finished lipid preparations were stored at 4° C. where they are stable for approximately 1 month.

Protein Labeling—Labeling of Cysteines in Solution: Recombinant His-tagged (N-terminus) H-Ras protein was prepared according to standard protocols (6). The Ras protein prepared according to this protocol is bound to GDP. The protein was then labeled with PyMPO-MALEIMIDE™ (1-(2-Maleimidylethyl)-4-(5-(4-Methoxyphenyl)Oxazol-2-yl) Pyridinium Methanesulfonate), a cysteine-reactive dye in 0.1 M Tris pH 8.0, 20 mM NaCl, 0.5 mM TCEP, 5% glycerol and a 12:1 dye:protein ratio for one hour at room temperature. Unreacted dye was purified away by gel filtration. The resulting dye:protein ratio was 0.7:1 and was determined spectrophotometrically. A single cysteine is solvent-accessible in the X-ray crystal structure of Ras (Cys 118); this observation is in accord with the measured dye:protein ratio being less than or equal to 1.0. Cysteine-labeled Ras was then coupled directly to the membrane.

Protein Labeling—Random Labeling of Amines in Solution: Amine groups in the Ras protein were labeled using a standard protocol in pH 8.3 sodium bicarbonate buffer (Invitrogen, Inc.) and purified by gel filtration and dialysis. Amine-labeled Ras was then coupled directly to the membrane.

Slide Preparation and Protein Loading: Immediately before applying DOPC/DGS NTA (Ni) lipids, microscope slides were cleaned with Piranha wash for 20 minutes and were then rinsed 3× with $diH_2O$ in a slide staining vessel. Slides were dried with compressed Nitrogen. SHG wells were assembled by attaching adhesive gaskets to Piranha-cleaned slides. dDOPC/DGS NTA (Ni) lipid preparation was diluted 1:1 with PBS or TBS buffers. 100 mM NaCl was required to reduce hydrostatic charge of the glass slide and enable the SLB to form. 10 μL of diluted DOPC/DGS NTA (Ni) lipid was pipetted into the wells of the slide followed by incubation for 5 minutes at room temperature. The wells were washed 2× by submersing the slide in buffer bath (PBS or TBS) and agitating with a 200 μL pipettor. Care was taken to ensure that no air was introduced into the wells at any time. A 1:1 volume of 100 mM $NiCl_2$ solution was added to all wells and incubated for 10 minutes at room temperature. The wells were washed 2× by submersing the slide in buffer bath (PBS or TBS) and agitating with a 200 μL pipettor. The buffer in the wells was then exchanged to the appropriate protein loading buffer.

A fluid supported lipid bilayer was confirmed by epifluorescence imaging the surface using Texas Red-DHPE. Lateral mobility of the bilayers was confirmed by fluorescence recovery after photobleaching, as known in the art. The target protein of interest was then loaded onto the wells and incubated 30 to 90 minutes at room temperature. The wells were rinsed thoroughly with assay buffer before starting experiments.

Results

Figure 3:
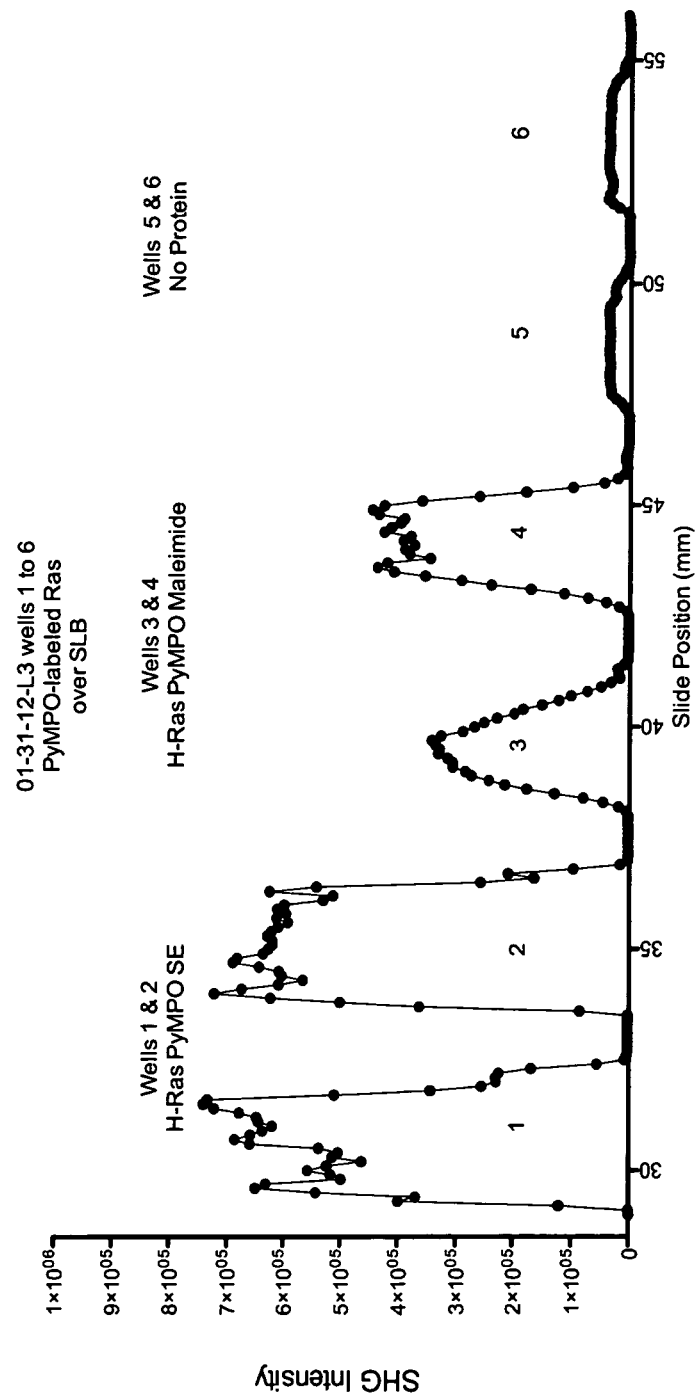
FIG. 3 depicts SHG data showing that labeled Ras protein can be detected by SHG on a supported lipid bilayer (SLB).

Labeled H-Ras protein (via amines or cysteines) was loaded onto the supported lipid bilayer (SLB) surface at 3 μM for 45 minutes, followed by washing. FIG. 3 shows that labeled protein can be detected by SHG on the SLB. If imidazole is added, the signal drops to the baseline level, indicating that attachment to the surface occurs via the protein's His-tag.

This example demonstrates that the Ras protein can be labeled on both native amine and sulfhydryl groups and coupled to a supported lipid bilayer via an N-terminal histidine affinity tag for detection using SHG technology.

Example 6

Detecting Conformational Changes at Two Different Sites in a Protein to Study Specificity of Agent Binding and Functionality of Protein Binding Sites This example demonstrates how detecting conformational change at two different sites in a protein provides information about the specificity of a binding agent. In this example, one site is a solvent-accessible cysteine in Ras (C118), as identified in solved X-ray crystal structures (PDB codes 3L8Z, 5P21, etc.) of the Ras protein. The other sites are sites with free amines (lysines). Several compounds are tested for their ability to change conformation in these two locations (cysteine site vs. amine sites). One compound produces conformational change at only the amine site and not the cysteine site, indicating that this compound binds specifically to Ras.

This example also demonstrates how it is possible to label and study functionally relevant sites in a protein: Cysteine 118 is near the catalytic region of Ras (the distance between the sulfur atom SG of the cysteine residue and the phosphate atom PA of the nucleotide in the 3L8Z structure is 1.6 nm and thus provides information about whether the compounds are capable of altering the conformation specifically in the catalytic region.

A panel of three small molecules was tested on randomly-labeled (amine labeled) and cysteine-labeled wildtype H-Ras protein tethered to an SLB surface via N-terminal 6× histidine tags.

Materials and Methods

PyMPO-SE™ (1-(3-(Succinimidyloxycarbonyl)Benzyl)-4-(5-(4-Methoxyphenyl)Oxazol-2-yl)Pyridinium Bromide) was coupled to His-tagged wildtype H-Ras (Novus) using one of two protocols.

In the first protocol, the protein was first bound to a supported lipid bilayer surface (DOPC with 3% Ni-NTA DOGS prepared via SUVs and a standard protocol known to those skilled in the art) and subsequently exposed to 10 μM PyMPO-SE™ (1(3-(Succinimidyloxycarbonyl)Benzyl)-4-(5-(4-Methoxyphenyl)Oxazol-2-yl)Pyridinium Bromide) for 30 minutes before washing.

Alternatively, Ras was labeled using a standard second protocol in pH 8.3 sodium bicarbonate buffer (Invitrogen, Inc.) and purified by gel filtration and dialysis. Labeled Ras was then coupled directly to the membrane. In the second protocol, H-Ras was labeled using a cysteine-reactive SHG probe, PyMPO-MALEIMIDE™ (1-(2-Maleimidylethyl)-4-(5-(4-Methoxyphenyl)Oxazol-2-yl)Pyridinium Methanesulfonate).

Recombinant His-tagged (N-terminus) H-Ras protein was prepared according to standard protocols (Hall et al., 2002, Proc. Nat. Acad. Sci., U.S.A., 99(19):12138-42). The Ras protein prepared according to this protocol is bound to GDP. The protein was then labeled with PyMPO-MALEIMIDE™ (1-(2-Maleimidylethyl)-4-(5-(4-Methoxyphenyl)Oxazol-2-yl)Pyridinium Methanesulfonate), a cysteine-reactive dye in 0.1 M Tris pH 8.0, 20 mM NaCl, 0.5 mM TCEP, 5% glycerol and a 12:1 dye:protein ratio for one hour at room temperature. Unreacted dye was purified away by gel filtration. The resulting dye:protein ratio was 0.7:1 as determined spectrophotometrically.

Three compounds were exposed to labeled Ras: Compound 1: 117028, 5-bromo-7-[(4-phenylpiperazin-1-yl)methyl]quinolin-8-ol; Compound 2: 643000, 2-(1H-imidazol-2-ylmethyl)-4-(1H-imidazol-4-ylmethyl)-1H-imidazole; and Compound 3: 662796, 1H-Pyrido[2,3-e][1,2,4][triazepin-1-one, 2,3-dihydro-4-[(morpholinoacetyl)amino].

Conformational change of immobilized Ras target was induced by addition of 5 µL of Compounds 1 to 3 separately at 3× concentration (30 µM) into 10 µL assay buffer over the wells followed by gentle mixing. The final concentration of each compound was 10 µM. Assay buffer was 20 mM Tris pH 8.0, 150 mM NaCl, 0.5 mM DTT, 0.15% DMSO.

Results

Figure 4A:
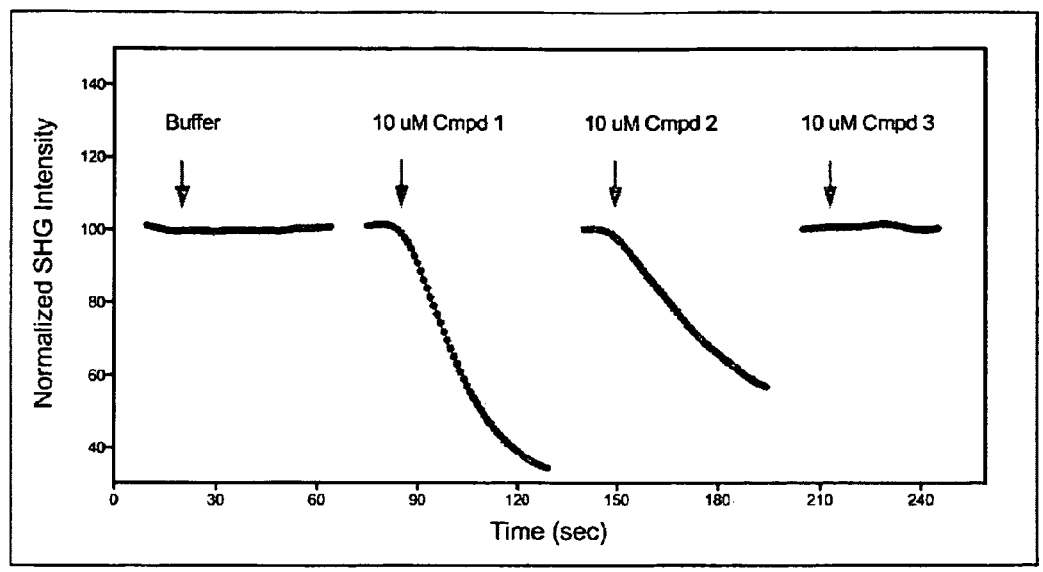
FIG. 4 depicts SHG data for binding of three compounds to amine-labeled (solution labeling) Ras target protein with A) showing normalized SHG intensity and B) depicting percent shift. Baseline SHG measurements were gathered for about 5 seconds before manually injecting each compound at a 2× concentration of 20 μM. Conformational change was monitored in real time for a period of about 60 seconds after injection.
Figure 4B:
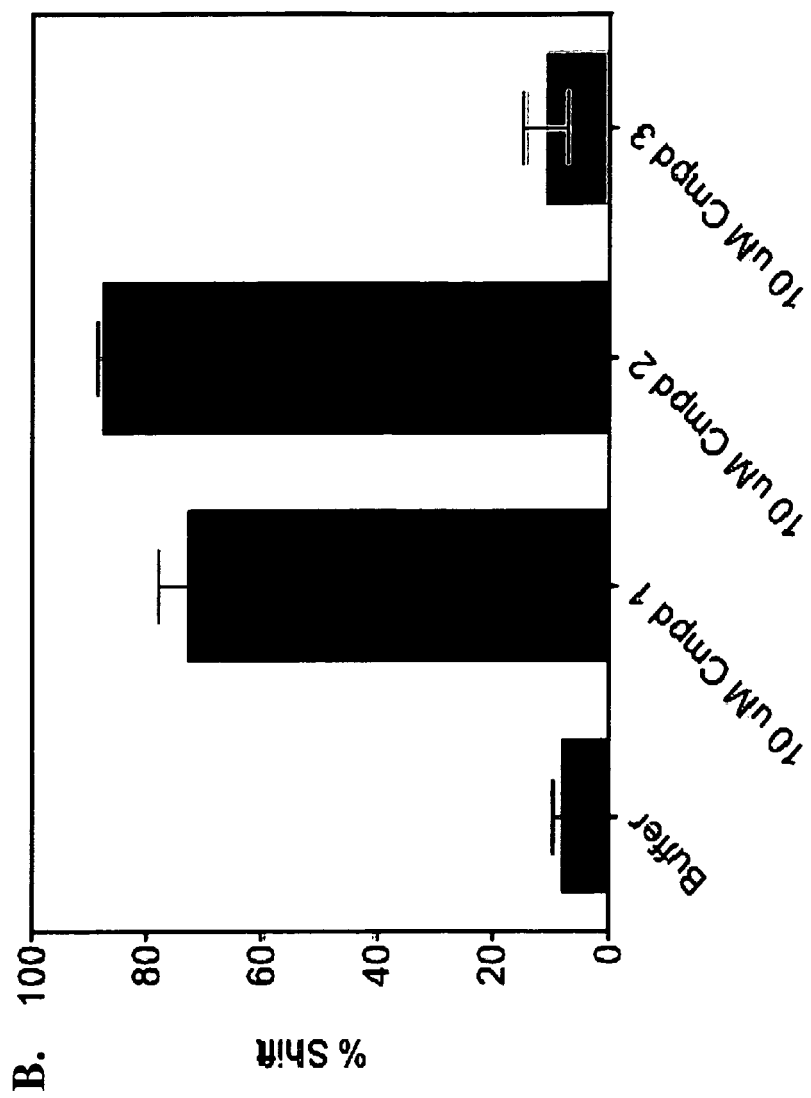
Figure 5A:
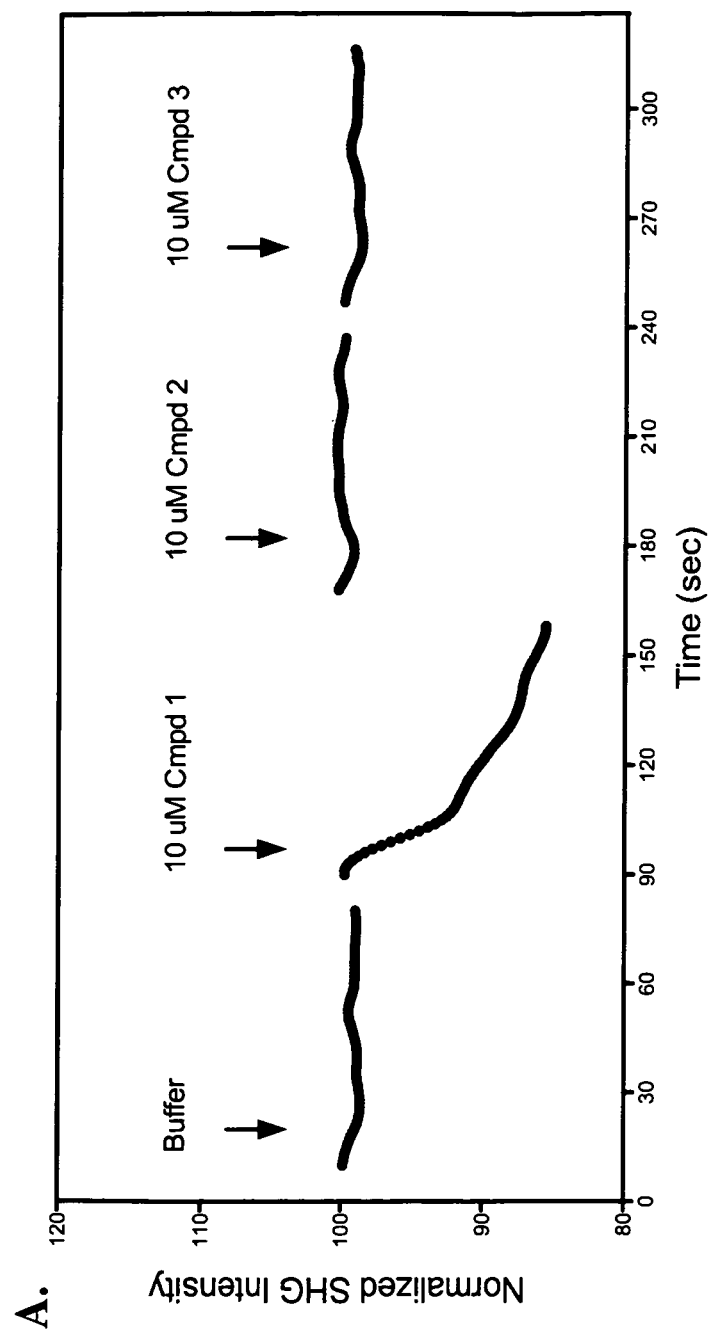
FIG. 5 depicts SHG data for binding of three compounds to cysteine-labeled Ras target protein with A) showing normalized SHG intensity and B) depicting percent shift. Baseline SHG measurements were gathered for about 5 seconds before manually injecting each compound at a 2× concentration of 20 μM. Conformational change was monitored in real time for a period of about 60 seconds after injection.
Figure 5B:
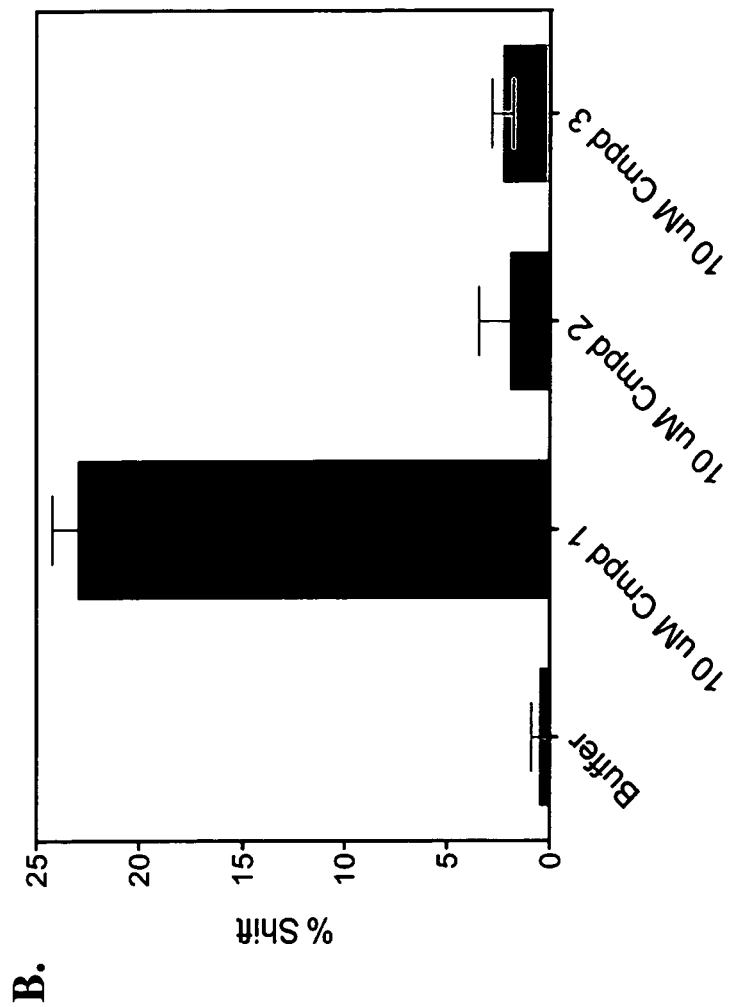

The results are summarized in Table 1. Compound 1 displayed activity on both the amine and cysteine-labeled protein, while Compound 2 only displayed activity on the amine-labeled protein. Compound 3 did not react with Ras protein, irrespective of the location of the label. PyMPO-SE™ (1-(3-(Succinimidyloxycarbonyl)Benzyl)-4-(5-(4-Methoxyphenyl)Oxazol-2-yl)Pyridinium Bromide) exposed to a blank bilayer (no protein) followed by washing led to no signal above background. Thus, the signal detected in the presence of protein after labeling is due to labeling of the protein itself while immobilized on the membrane. The site-dependent activity of Compound 2 provides additional support for its specific binding to the protein. Compound 1, because it has activity at the functionally relevant cysteine site, is likely to have an effect on the catalytic region nearby (nm away). FIG. 4 shows data for the amine-labeled H-Ras target. FIG. 5 shows data for the cysteine-labeled H-Ras target. Baseline SHG measurements were gathered for about 5 seconds before manually injecting each compound at a 2× concentration of 20 µM. Conformational change was monitored in real time for a period of about 60 seconds after injection. Differential activities of the applied compounds were observed dependent on the placement of the probes on amine or cysteine sites.

TABLE 1

Summary table of compound activity on H-Ras labeled by the two different methods described in the text.

| | SHG: Conformation change | |
| --- | --- | --- |
| | Cysteine-labeled | Amine-labeled |
| Compound 1 | + | +++ |
| Compound 2 | − | +++ |
| Compound 3 | − | − |

This experiment demonstrates that SHG can be used to identify small molecule chemical compounds capable of inducing a conformational change in the structure of a Ras protein tethered to a supported lipid bilayer.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

1. Christopoulos A. Allosteric binding sites on cell-surface receptors: novel targets for drug discovery. Nat Rev Drug Discov. 2002; 1(3):198-210.
2. Schneider E, Keller M, Brennauer A, Hoefelschweiger B K, Gross D, Wolfbeis O S, et al. Synthesis and Characterization of the First Fluorescent Nonpeptide NPY Y1 Receptor Antagonist. ChemBioChem. 2007; 8(16):1981-8.
3. Campagnola P J, Loew L M. Second harmonic imaging microscopy for visualizing biomolecular arrays in cells, tissues and organisms. Nature Biotechnology. 2003;21(11):1356-60.
4. Millard A C, Campagnola P J, Mohler W, Lewis A, Loew L M. Second harmonic imaging microscopy. Biophotonics, Pt B 2003. p. 47-69.
5. Shan Y B, Seeliger M A, Eastwood M P, Frank F, Xu H F, Jensen M O, et al. A conserved protonation-dependent switch controls drug binding in the Abl kinase. Proceedings of the National Academy of Sciences of the United States of America. 2009; 106(1):139-44.
6. Seeliger M A, Ranjitkar P, Kasap C, Shan Y B, Shaw D E, Shah N P, et al. Equally Potent Inhibition of c-Src and Abl by Compounds that Recognize Inactive Kinase Conformations. Cancer Research. 2009; 69(6):2384-92.
7. Seeliger M A, Young M, Henderson M N, Pellicena P, King D S, Falick A M, et al. High yield bacterial expression of active c-Abl and c-Src tyrosine kinases. Protein Science. 2005; 14(12):3135-9.
8. Nagar B, Hantschel O, Young M A, Scheffzek K, Veach D, Bornmann V, et al. Structural basis for the autoinhibition of c-Abl tyrosine kinase. Cell. 2003; 112(6):859-71.
9. Seeliger M A, Nagar B, Frank F, Cao X, Henderson M N, Kuriyan J. c-Src binds to the cancer drug imatinib with an inactive Abl/c-Kit conformation and a distributed thermodynamic penalty. Structure. 2007; 15:299-311.
10. Hall B E, Bar-Sagi D, Nassar N. The structural basis for the transition from Ras-GTP to Ras-GDP. Proceedings of the National Academy of Sciences. 2002; 99(19):12138-42.
11. Rajagopalan P T R, Zhang Z, McCourt L, Dwyer M, Benkovic S J, Hammes G G. Interaction of dihydrofolate reductase with methotrexate: Ensemble and single-molecule kinetics. Proceedings of the National Academy of Sciences of the United States of America. 2002; 99(21): 13481-6.

12. Goodey N M, Benkovic S J. Allosteric regulation and catalysis emerge via a common route. Nat Chem Biol. 2008; 4(8):474-82.
13. Antikainen N M, Smiley R D, Benkovic S J, Hammes G G. Conformation Coupled Enzyme Catalysis:, Ää Single-Molecule and Transient Kinetics Investigation of Dihydrofolate Reductase, Ä†. Biochemistry. 2005; 44(51):16835-43.
14. Nagar B, et al. Structural basis for the autoinhibition of c-Abl tyrosine kinase. Cell 2003; 112(6):859-871.
15. Harrison S C. Variation on an Src-like Theme. *Cell* 2003; 112(6):737-740.

The invention claimed is:

1. A method of determining a binding interaction between a target biomolecule and a candidate binding partner comprising:
   a. labeling the target biomolecule at a first site with a first second harmonic-active moiety having a net orientation at an interface; contacting the target biomolecule with the candidate binding partner; and detecting a first detectable signal upon binding between the target biomolecule and the candidate binding partner; wherein the first detectable signal is generated by the second harmonic-active moiety using a surface selective technique;
   b. separately labeling the target biomolecule at a second site with a second second harmonic-active moiety having a net orientation at an interface; contacting the target biomolecule with the candidate binding partner; and detecting a second detectable signal upon binding between the target biomolecule and the candidate binding partner; wherein the second detectable signal is generated by the second harmonic-active moiety using a surface selective technique;
   c. comparing the first detectable signal with the second detectable signal, wherein a difference between the first detectable signal and the second detectable signal indicates a binding interaction between the target biomolecule and the candidate binding partner.

2. The method of claim 1, wherein the second harmonic-active moiety is selected from the group consisting of PyMPO maleimide, PyMPO-NHS, PyMPO-succinimidyl ester, Badan, and Acrylodan.

3. The method of claim 1, wherein the second harmonic-active moiety is bound to the target bimolecule by one or more sulfhydryl groups on the surface of the target bimolecule.

4. The method of claim 3, wherein said one or more sulfhydryl groups are native sulfhydryl groups.

5. The method of claim 3, wherein said one or more sulfhydryl groups are engineered sulfhydryl groups.

6. The method of claim 2, wherein the second harmonic-active moiety is bound to the target bimolecule by one or more amine groups on the surface of the target bimolecule.

7. The method of claim 6, wherein said one or more amine groups are native amine groups.

8. The method of claim 6, wherein said one or more amine groups are engineered amine groups.

9. The method of claim 1, wherein the target biomolecule is labeled in situ while bound to a surface.

10. The method of claim 1, wherein the second harmonic-active moiety is an unnatural amino acid.

11. The method of claim 10, wherein the unnatural amino acid is Aladan.

12. The method of claim 1, wherein the first site and the second site is within a binding interface of the target biomolecule.

13. The method of claim 1, wherein the first site and the second site is outside a binding interface of the target biomolecule.

14. The method of claim 1, wherein the first site is within a binding interface of the target biomolecule and the second site is outside the binding interface of the target biomolecule.

15. The method of claim 1, wherein the target biomolecule is a protein, a DNA molecule, an RNA molecule or an oligosaccharide.

16. The method of claim 1, wherein the interface is selected from the group consisting of:
   a glass surface, a polyethylene glycol surface, a supported lipid bilayer surface, a lipid analog bilayer surface, a plastic surface, a metal surface, a latex surface, a rubber surface, a ceramic surface, a polymeric surface, a polypropylene surface, a polyvinylidene difluoride surface, a polyethylene surface.

17. The method of claim 16, wherein the interface is derivatized with oligo-PEG molecules or lipids.

18. The method of claim 17, wherein the oligo-PEG molecules or lipids are Ni-NTA-bearing oligo-PEG molecules or Ni-NTA-bearing lipids.

19. The method of claim 1, wherein the target bimolecule comprises an affinity tag.

20. The method of claim 1, wherein the difference between the first detectable signal and the second detectable signal is a difference above a noise level.

21. The method of claim 20, wherein the difference above the noise level between the first detectable signal and the second detectable signal indicates a specific binding interaction between the target biomolecule and the candidate binding partner.

* * * * *